United States Patent
Achiluzzi et al.

(10) Patent No.: US 11,819,406 B2
(45) Date of Patent: Nov. 21, 2023

(54) LOADING SYSTEM FOR AN IMPLANTABLE PROSTHESIS AND RELATED LOADING METHOD

(71) Applicant: Corcym S.r.l., Milan (IT)

(72) Inventors: Monica Francesca Achiluzzi, Saluggia (IT); Giovanni Giordano, Saluggia (IT); Felice Giuseppe Carlino, Saluggia (IT)

(73) Assignee: Corcym S.r.l., Milan (IT)

( * ) Notice: Subject to any disclaimer, the term of this patent is extended or adjusted under 35 U.S.C. 154(b) by 403 days.

(21) Appl. No.: 17/057,523

(22) PCT Filed: May 23, 2018

(86) PCT No.: PCT/IB2018/053648
§ 371 (c)(1),
(2) Date: Nov. 20, 2020

(87) PCT Pub. No.: WO2019/224582
PCT Pub. Date: Nov. 28, 2019

(65) Prior Publication Data
US 2021/0196460 A1     Jul. 1, 2021

(51) Int. Cl.
*A61F 2/24*     (2006.01)
*A61F 2/95*     (2013.01)
*A61F 2/00*     (2006.01)

(52) U.S. Cl.
CPC .......... *A61F 2/2436* (2013.01); *A61F 2/0095* (2013.01); *A61F 2/9525* (2020.05)

(58) Field of Classification Search
CPC .... A61F 2/2436; A61F 2/0095; A61F 2/9525; A61F 2/9522
See application file for complete search history.

(56) References Cited

U.S. PATENT DOCUMENTS

| | | |
|---|---|---|
| 3,363,442 A | 1/1968 | Kennedy et al. |
| 3,409,013 A | 11/1968 | Henry et al. |
| 4,683,883 A | 8/1987 | Martin |
| 5,042,161 A | 8/1991 | Hodge |
| 5,360,014 A | 11/1994 | Sauter et al. |
| 5,489,296 A | 2/1996 | Love et al. |
| 5,522,884 A | 6/1996 | Wright |
| 5,560,487 A | 10/1996 | Starr |
| 5,669,919 A | 9/1997 | Sanders et al. |

(Continued)

FOREIGN PATENT DOCUMENTS

| | | |
|---|---|---|
| DE | 29911694 U1 | 8/1999 |
| DE | 102004019254 B3 | 7/2005 |

(Continued)

OTHER PUBLICATIONS

International Search Report and Written Opinion for International Application No. PCT/IB2018/053648, dated Feb. 13, 2019, 8 pages.

*Primary Examiner* — Thomas McEvoy
(74) *Attorney, Agent, or Firm* — Eversheds Sutherland (US) LLP; Christopher C. Bolten; Joshua W. Branson

(57) ABSTRACT

Disclosed herein is a loading system (1) for implantable prostheses, specifically heart valve prostheses. The loading system (1) may be pre-mounted in a storage container (J) filled with a preservation solution with the prosthesis attached thereto, and may provide one or more deployment elements of a delivery instrument as receivers (4, 33) for the loading of the prosthesis (2).

16 Claims, 15 Drawing Sheets

(56) References Cited

U.S. PATENT DOCUMENTS

| | | |
|---|---|---|
| 5,672,169 A | 9/1997 | Verbeek |
| 5,693,066 A | 12/1997 | Rupp et al. |
| 5,698,307 A | 12/1997 | Levy |
| 5,776,187 A | 7/1998 | Krueger et al. |
| 5,800,531 A | 9/1998 | Cosgrove et al. |
| 5,810,873 A | 9/1998 | Morales |
| 5,814,096 A | 9/1998 | Lam et al. |
| 5,824,068 A | 10/1998 | Bugge |
| 5,885,228 A | 3/1999 | Rosenman et al. |
| 5,947,993 A | 9/1999 | Morales |
| 5,951,540 A | 9/1999 | Verbeek |
| 5,972,016 A | 10/1999 | Morales |
| 6,019,739 A | 2/2000 | Rhee et al. |
| 6,024,737 A | 2/2000 | Morales |
| 6,051,002 A | 4/2000 | Morales |
| 6,063,102 A | 5/2000 | Morales |
| 6,110,200 A | 8/2000 | Hinnenkamp |
| 6,202,272 B1 | 3/2001 | Jackson |
| 6,214,043 B1 | 4/2001 | Krueger et al. |
| 6,277,110 B1 | 8/2001 | Morales |
| 6,309,383 B1 | 10/2001 | Campbell et al. |
| 6,350,281 B1 | 2/2002 | Rhee |
| 6,352,547 B1 | 3/2002 | Brown et al. |
| 6,387,117 B1 | 5/2002 | Arnold, Jr. et al. |
| 6,402,780 B2 | 6/2002 | Williamson, IV et al. |
| 6,454,799 B1 | 9/2002 | Schreck |
| 6,481,262 B2 | 11/2002 | Ching et al. |
| 6,506,201 B2 | 1/2003 | Di Caprio et al. |
| 6,510,722 B1 | 1/2003 | Ching et al. |
| 6,598,307 B2 | 7/2003 | Love et al. |
| 6,629,350 B2 | 10/2003 | Motsenbocker |
| 6,678,962 B1 | 1/2004 | Love et al. |
| 6,726,713 B2 | 4/2004 | Schaldach et al. |
| 6,730,118 B2 | 5/2004 | Spenser et al. |
| 6,769,161 B2 | 8/2004 | Brown et al. |
| 6,846,324 B2 | 1/2005 | Stobie |
| 6,915,560 B2 | 7/2005 | Austin |
| 6,966,924 B2 | 11/2005 | Holmberg |
| 6,968,607 B2 | 11/2005 | Motsenbocker |
| 6,981,982 B2 | 1/2006 | Armstrong et al. |
| 6,988,881 B2 | 1/2006 | Motsenbocker et al. |
| 7,007,396 B2 | 3/2006 | Rudko et al. |
| 7,021,114 B2 | 4/2006 | Perreault |
| 7,069,794 B2 | 7/2006 | Motsenbocker et al. |
| 7,258,698 B2 | 8/2007 | Lemmon |
| 7,338,484 B2 | 3/2008 | Schoon et al. |
| 7,357,814 B2 | 4/2008 | Gabbay |
| 7,367,984 B2 | 5/2008 | Kulcinski et al. |
| 7,389,874 B2 | 6/2008 | Quest et al. |
| 7,427,291 B2 | 9/2008 | Liddicoat et al. |
| 8,006,535 B2 | 8/2011 | Righini et al. |
| 8,747,458 B2 | 6/2014 | Tuval et al. |
| 9,114,010 B2 | 8/2015 | Gaschino et al. |
| 9,585,752 B2 | 3/2017 | Chang et al. |
| 2001/0049558 A1 | 12/2001 | Liddicoat et al. |
| 2002/0035390 A1 | 3/2002 | Schaldach et al. |
| 2002/0042651 A1 | 4/2002 | Liddicoat et al. |
| 2002/0129820 A1 | 9/2002 | Ryan et al. |
| 2002/0198594 A1 | 12/2002 | Schreck |
| 2003/0114913 A1 | 6/2003 | Spenser et al. |
| 2003/0125805 A1 | 7/2003 | Johnson et al. |
| 2003/0192134 A1 | 10/2003 | Desenne et al. |
| 2003/0192164 A1 | 10/2003 | Austin |
| 2004/0039436 A1 | 2/2004 | Spenser et al. |
| 2004/0123437 A1 | 7/2004 | Kokish |
| 2004/0193259 A1 | 9/2004 | Gabbay |
| 2004/0225356 A1 | 11/2004 | Frater |
| 2005/0166389 A1 | 8/2005 | Perreault et al. |
| 2005/0197695 A1 | 9/2005 | Stacchino et al. |
| 2005/0197696 A1 | 9/2005 | Gomez Duran |
| 2005/0229670 A1 | 10/2005 | Perreault |
| 2005/0234537 A1 | 10/2005 | Edin |
| 2005/0240256 A1 | 10/2005 | Austin |
| 2005/0267529 A1 | 12/2005 | Crockett et al. |
| 2005/0283232 A1 | 12/2005 | Gabbay |
| 2006/0004469 A1 | 1/2006 | Sokel |
| 2006/0074486 A1 | 4/2006 | Liddicoat et al. |
| 2006/0178470 A1 | 8/2006 | Majolo et al. |
| 2006/0178740 A1 | 8/2006 | Stacchino et al. |
| 2006/0265855 A1 | 11/2006 | Stenzel |
| 2007/0027534 A1 | 2/2007 | Bergheim et al. |
| 2007/0056346 A1 | 3/2007 | Spenser et al. |
| 2007/0061009 A1 | 3/2007 | Spenser et al. |
| 2007/0100356 A1 | 5/2007 | Lucatero et al. |
| 2007/0162113 A1 | 7/2007 | Sharkawy et al. |
| 2007/0173861 A1 | 7/2007 | Strommer et al. |
| 2008/0262603 A1 | 10/2008 | Giaquinta et al. |
| 2009/0018570 A1 | 1/2009 | Righini et al. |
| 2009/0054976 A1 | 2/2009 | Tuval et al. |
| 2009/0192603 A1 | 7/2009 | Ryan |
| 2010/0049313 A1 | 2/2010 | Alon et al. |
| 2010/0249661 A1 | 9/2010 | Righini et al. |
| 2010/0252470 A1 | 10/2010 | Ryan et al. |
| 2010/0262043 A1 | 10/2010 | Sauter et al. |
| 2010/0292779 A1 | 11/2010 | Straubinger et al. |
| 2012/0271398 A1 | 10/2012 | Essinger et al. |
| 2014/0260097 A1 | 9/2014 | Avery et al. |
| 2015/0018938 A1 | 1/2015 | Von Segesser et al. |
| 2016/0354205 A1 | 12/2016 | Essinger et al. |

FOREIGN PATENT DOCUMENTS

| | | |
|---|---|---|
| DE | 102004019254 B8 | 11/2005 |
| DE | 202011000848 U1 | 6/2011 |
| EP | 0095970 A2 | 12/1983 |
| EP | 0778009 A2 | 6/1997 |
| EP | 0778009 B1 | 7/2002 |
| EP | 1353420 B1 | 3/2005 |
| EP | 2520251 A1 | 11/2012 |
| EP | 3034014 A2 | 6/2016 |
| GB | 2083362 A | 3/1982 |
| JP | H11332997 A | 12/1999 |
| JP | 2004154164 A | 6/2004 |
| WO | WO-9639942 A1 | 12/1996 |
| WO | WO-9724989 A1 | 7/1997 |
| WO | WO-9814138 A1 | 4/1998 |
| WO | WO-9953864 A1 | 10/1999 |
| WO | WO-9953866 A1 | 10/1999 |
| WO | WO-9955255 A1 | 11/1999 |
| WO | WO-0006052 A1 | 2/2000 |
| WO | WO-0021464 A1 | 4/2000 |
| WO | WO-0030565 A1 | 6/2000 |
| WO | WO-0119768 A2 | 3/2001 |
| WO | WO-0121076 A1 | 3/2001 |
| WO | WO-0121097 A2 | 3/2001 |
| WO | WO-0121103 A2 | 3/2001 |
| WO | WO-0121110 A1 | 3/2001 |
| WO | WO-0176510 A2 | 10/2001 |
| WO | WO-0176510 A8 | 1/2002 |
| WO | WO-0211646 A1 | 2/2002 |
| WO | WO-0121103 A9 | 10/2002 |
| WO | WO-02092257 A1 | 11/2002 |
| WO | WO-2005082578 A1 | 9/2005 |
| WO | WO-2006088712 A1 | 8/2006 |
| WO | WO-2006117016 A1 | 11/2006 |
| WO | WO-2006127089 A1 | 11/2006 |
| WO | WO-2006136930 A1 | 12/2006 |
| WO | WO-2007030825 A2 | 3/2007 |
| WO | WO-2007030825 A3 | 6/2007 |
| WO | WO-2006007401 A3 | 1/2008 |
| WO | WO-2008008365 A2 | 1/2008 |
| WO | WO-0121097 A3 | 3/2008 |
| WO | WO-2008089365 A2 | 7/2008 |
| WO | WO-2009091509 A1 | 7/2009 |
| WO | WO-2009108942 A1 | 9/2009 |
| WO | WO-2010112608 A1 | 10/2010 |
| WO | WO-2010130789 A1 | 11/2010 |
| WO | WO-2012106491 A1 | 8/2012 |
| WO | WO-2016046599 A1 | 3/2016 |

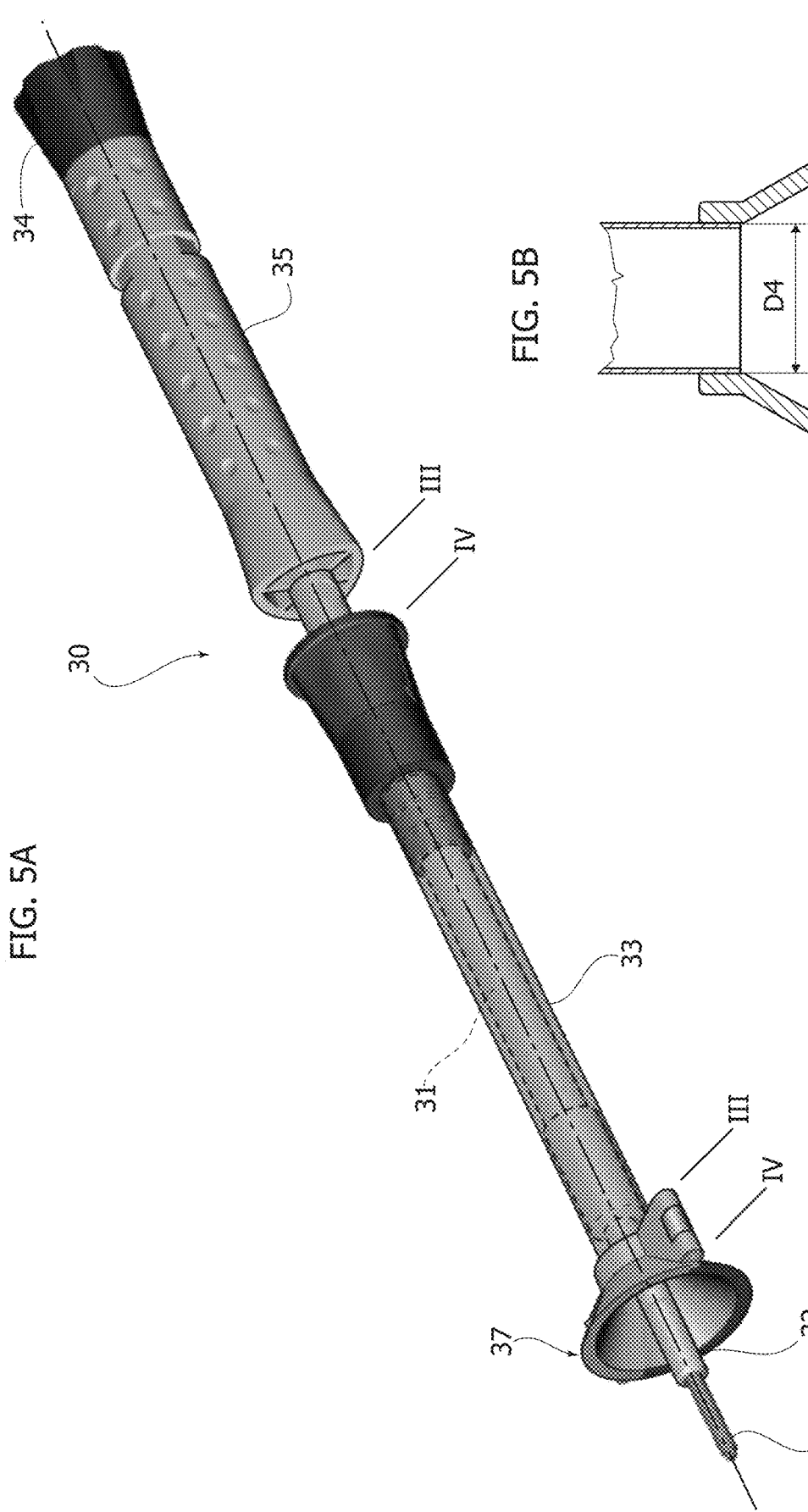
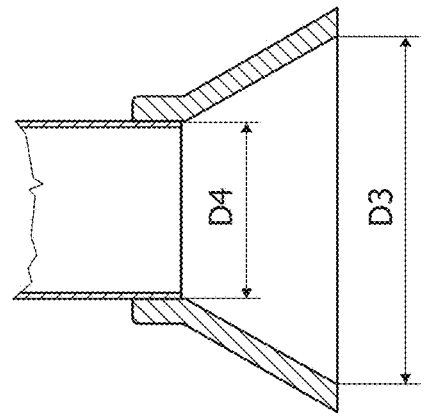
FIG. 5A
FIG. 5B

LOADING SYSTEM FOR AN IMPLANTABLE PROSTHESIS AND RELATED LOADING METHOD

CROSS REFERENCE TO RELATED APPLICATIONS

This application is a national stage application of PCT/IB2018/053648 filed May 23, 2018, which is herein incorporated by reference in its entirety.

TECHNICAL FIELD

The present disclosure refers to implantable prostheses loading systems and methods, and in particular, to implantable prostheses loading systems for heart valve prostheses including a radially contractible armature and a heart valve prosthesis carried by the armature.

BACKGROUND

In the fields of heart valve surgery and interventional cardiology, easy handling of implantable prostheses such as vascular prostheses and heart valve prostheses, and the reduction of the time required to perform a surgical intervention and procedure are main topics of the medical and technological research in the field.

With reference to the implantation of expandable heart valve prostheses, such as for example sutureless valve prostheses, a current practice provides that a heart valve prosthesis should be stored in a sterile environment to maintain its integrity.

Loading an implantable heart valve prosthesis onto a delivery instrument may present a number of important issues. While many crimping devices with different features have been devised to facilitate the crimping operation, such a step may remain rather delicate and complex to perform.

One of the major challenges for the practitioner when loading a heart valve prosthesis onto a delivery instrument, is the handling of the prosthesis from the storage facility (typically a so-called "jar" filled with a sterile solution for preservation) to the delivery instrument. Various current solutions require either multiple handling devices or even manual manipulation of the valve, which are both indeed undesirable under the prospect of an easy and flawless valve loading onto the delivery instrument.

SUMMARY

In embodiments, the challenges described above may be achieved by providing a system which renders loading of implantable heart valve prostheses onto a delivery instrument easier, safer, faster and more accurate in comparison to known systems.

In a first example, a loading system for a heart valve prosthesis including a radially contractible armature and a prosthetic heart valve coupled to said armature, said armature having at least one radially contractible annular portion, the loading system comprising:

a gripper that is axially operable along a longitudinal axis of the loading system from a first axial position to a second axial position, wherein in the first axial position the gripper engages the heart valve prosthesis with the armature in a radially expanded condition;

a first receiver for the heart valve prosthesis, the first receiver configured for holding at least a first portion of the heart valve prosthesis in a radially contracted condition upon engagement of the first receiver by the heart valve prosthesis, and wherein the gripper is axially displaceable relative to the first receiver; and a first funnel shaped element surrounding the first receiver, the first funnel shaped element having a first diameter and a second diameter, the second diameter being smaller than the first diameter and being arranged axially closer to the first receiver than the first diameter, and wherein the gripper is axially displaceable relative to the first funnel shaped element, wherein in a transition from the first axial position to the second axial position the gripper is configured to displace the heart valve prosthesis axially through the first funnel shaped element from the first diameter to the second diameter, so as to provide a radial contraction of the armature of the heart valve prosthesis and a fitting of said at least a first portion into said first receiver in a radially contracted condition upon reaching the second axial position.

A second example according to the first example, including a tubular member which is axially fixed relative to said gripper, the tubular member including a holder to which the first receiver is mated.

A third example according to the second example, wherein the gripper includes a stud encased by said tubular member and a gripping portion at one end of the stud, the tubular member further including a drive member engaging the stud to provide an axial displacement thereof upon operation of the drive member, the gripping portion engaging coupling elements of the at least a first portion of the heart valve prosthesis in the first axial position.

A fourth example according to the third example, wherein the stud is threaded, and wherein the drive member is a threaded rotary drive member engaging the thread of the stud.

A fifth example according to the second example or the third example, wherein said stud is a hollow stud and includes an axial slot, wherein the holder extends axially along and coaxially to the longitudinal axis and within the tubular member, wherein the hollow stud is slidably fitted around the holder, and wherein the axial slot accommodates a bridge member connecting the holder to the tubular member.

A sixth example according to any of the previous claims, wherein the gripper includes a gripping portion comprising a plurality of resilient finger members, the resilient finger members engaging the heart valve prosthesis radially outwardly of the same, and being radially displaceable from a radially divaricated condition to a radially collapsed condition upon an axial displacement of the gripper relative to the first funnel shaped element from the first axial position to the second axial position, thereby providing the radial contraction of the armature of the heart valve prosthesis.

A seventh example according to the sixth example, wherein each resilient finger is associated to a guide blade, each guide blade including a longitudinal through slot configured to accommodate the resilient finger during a displacement of the same from the radially divaricated to the radially collapsed condition, thereby keeping the same aligned along a longitudinal direction.

An eighth example according to any of the previous claims, wherein the first funnel shaped element is detachably coupled to the first receiver.

A ninth example according to any of the previous claims, comprising a delivery instrument for the heart valve prosthesis, the delivery instrument including a shaft, a hub coupled to said shaft, and a second receiver which is axially slidable relative to the hub from a third axial position to a fourth axial position, wherein:

the hub of the delivery instrument is configured for coupling with the first receiver;

the second receiver includes a second funnel shaped element coupled thereto, the second funnel shaped element having a third diameter and a fourth diameter, the fourth diameter being smaller than the third diameter and being axially closer to the second receiver than the third diameter, the third diameter being presented with the heart valve prosthesis coupled to the gripper; and in an axial displacement of the second receiver from the third axial position to the fourth axial position the second funnel shaped element moves relative to the heart valve prosthesis so that a second portion of the armature negotiates a lumen narrowing from the third diameter to the fourth diameter, and fits into the second receiver in a radially contracted condition.

A tenth example according to the ninth example, wherein the second funnel shaped element is detachably coupled to the second receiver.

An eleventh example according to the second example or the tenth example, wherein the first receiver is detachably coupled to the holder.

A twelfth example according to the first example, wherein the receiver, the gripper, and the heart valve prosthesis attached thereto are stored in a jar filled with a preservation solution, the first funnel shaped element being pre-mounted on the first receiver.

A thirteenth example according to the first or the twelfth example, wherein the loading system further includes a heart valve prosthesis including a radially contractible armature and a prosthetic heart valve carried by said armature, said armature having at least one radially contractible annular portion, wherein in the first axial position the gripper engages the heart valve prosthesis with the armature in a radially expanded condition.

A fourteenth example of a method of loading a prosthetic heart valve onto a delivery instrument using the loading system according to any of the previous examples, the method including:

displacing the gripper from the first axial position to the second axial position to fit the at least one portion of the heart valve prosthesis into the first receiver in a radially collapsed condition;

decoupling the first funnel shaped element from the loading system;

coupling the first receiver to the hub of the delivery instrument;

displacing the second receiver from the third axial position to the fourth axial position to fit the second portion of the heart valve prosthesis into the second receiver in a radially collapsed condition;

decoupling the second funnel shaped element from the delivery instrument;

decoupling the first receiver from the holder, while maintaining the first receiver attached to the hub of the delivery instrument.

A fifteenth example according to the fourteenth example, wherein decoupling the first receiver from the holder comprises axially displacing the gripper, with the at least a portion of the prosthesis loaded into the first receiver, back towards the first axial position to release the gripper from the prosthesis.

A sixteenth example according to the fifteenth example, wherein in the second axial position the resilient fingers are located axially outside of the first receiver and held in a radially contracted condition by the tubular member, wherein axially displacing the gripper back towards the first axial position releases the resilient fingers from the radial contraction action of the tubular member, thereby releasing the resilient fingers from coupling elements of the at least a first portion of the heart valve prosthesis with a radially outward motion thereof relative to the coupling elements.

A seventeenth example of a method of loading a prosthetic heart valve onto a delivery instrument using the loading system according to any of examples first to thirteenth, the method including:

displacing the gripper from the first axial position to the second axial position to fit the heart valve prosthesis into the first receiver in a radially collapsed condition;

decoupling the first funnel shaped element from the loading system, detaching the first receiver and coupling the same to a delivery instrument.

An eighteenth example according to the seventeenth example, wherein the first receiver includes an annular portion extended in length as a delivery sheath, and axially slidable relative to a hub, the annular portion extended in length being configured to cover the axial extension of the prosthesis.

A nineteenth example according to the eighteenth example, wherein the annular portion is intended to mate with actuation member of the delivery instrument for axial displacement thereof, and the hub is intended to mate with a static portion of a shaft of the delivery instrument.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

BRIEF DESCRIPTION OF THE FIGURES

Various embodiments herein will now be described with reference to the attached figures, provided purely by way of non-limiting example, wherein:

FIG. 5A illustrates a further component of the loading system, according to embodiments of the disclosure;

FIG. 5B is a schematic view of a portion thereof, according to embodiments of the disclosure.

Figure 1:
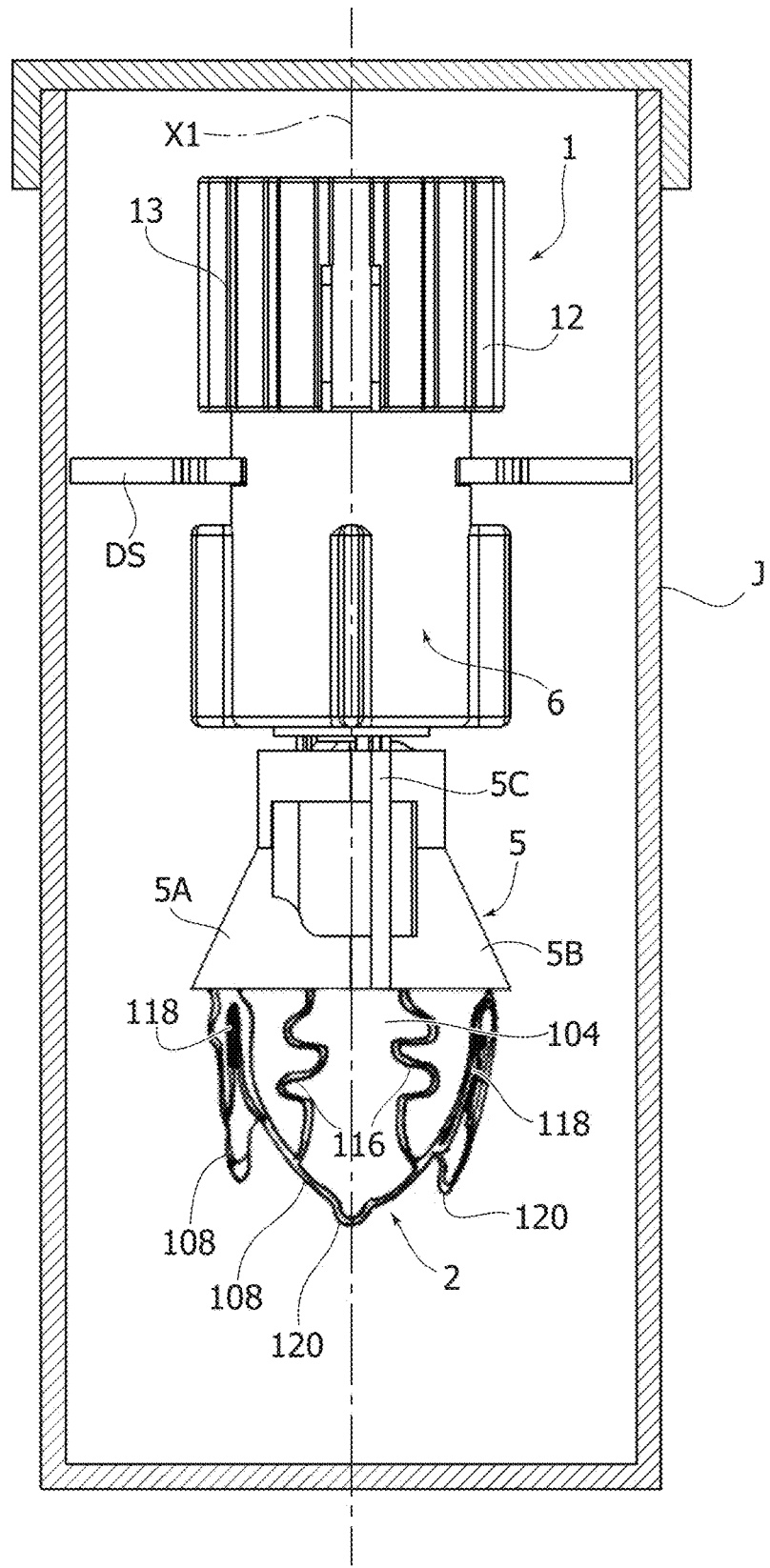
FIG. 1 is a perspective view of a loading system in a storage container, according to embodiments of the disclosure.

While the disclosure is amenable to various modifications and alternative forms, specific embodiments have been shown by way of example in the drawings and are described in detail below. The intention, however, is not to limit the disclosure to the embodiments described. On the contrary, the disclosure is intended to cover all modifications, equivalents, and alternatives falling within the scope of the disclosure as defined by the claims.

DETAILED DESCRIPTION

Reference number 1 in FIG. 1 designates a loading system for a heart valve prosthesis, according to embodiments of this disclosure.

In embodiments described herein, see FIGS. 1, 2A, 2B, and 3A, the loading system 1 may include:

a heart valve prosthesis 2 including a radially contractible armature and a prosthetic heart valve coupled to the armature, wherein the armature has at least one radially contractible annular portion;

a gripper 3 that is axially operable along a longitudinal axis X1 of the loading system 1 from a first axial position to a second axial position, wherein in the first axial position the gripper 3 engages the heart valve prosthesis 2 with the armature in a radially expanded condition;

a first receiver 4 for the heart valve prosthesis 2, the first receiver 4 being configured for holding a first portion, preferably the radially contractible annular portion, of the heart valve prosthesis 2 in a radially contracted condition upon engagement of the first receiver by the heart valve prosthesis, and wherein the gripper 3 is axially displaceable relative to the first receiver 4; and a first funnel shaped element 5 surrounding the first receiver 4, the first funnel shaped element 5 having a first diameter D1 and a second diameter D2, the second diameter being smaller than the first diameter and being arranged axially closer to the first receiver 4 than the first diameter D1, and wherein the gripper 3 is axially displaceable relative to the first funnel shaped element 5.

Figure 2A:
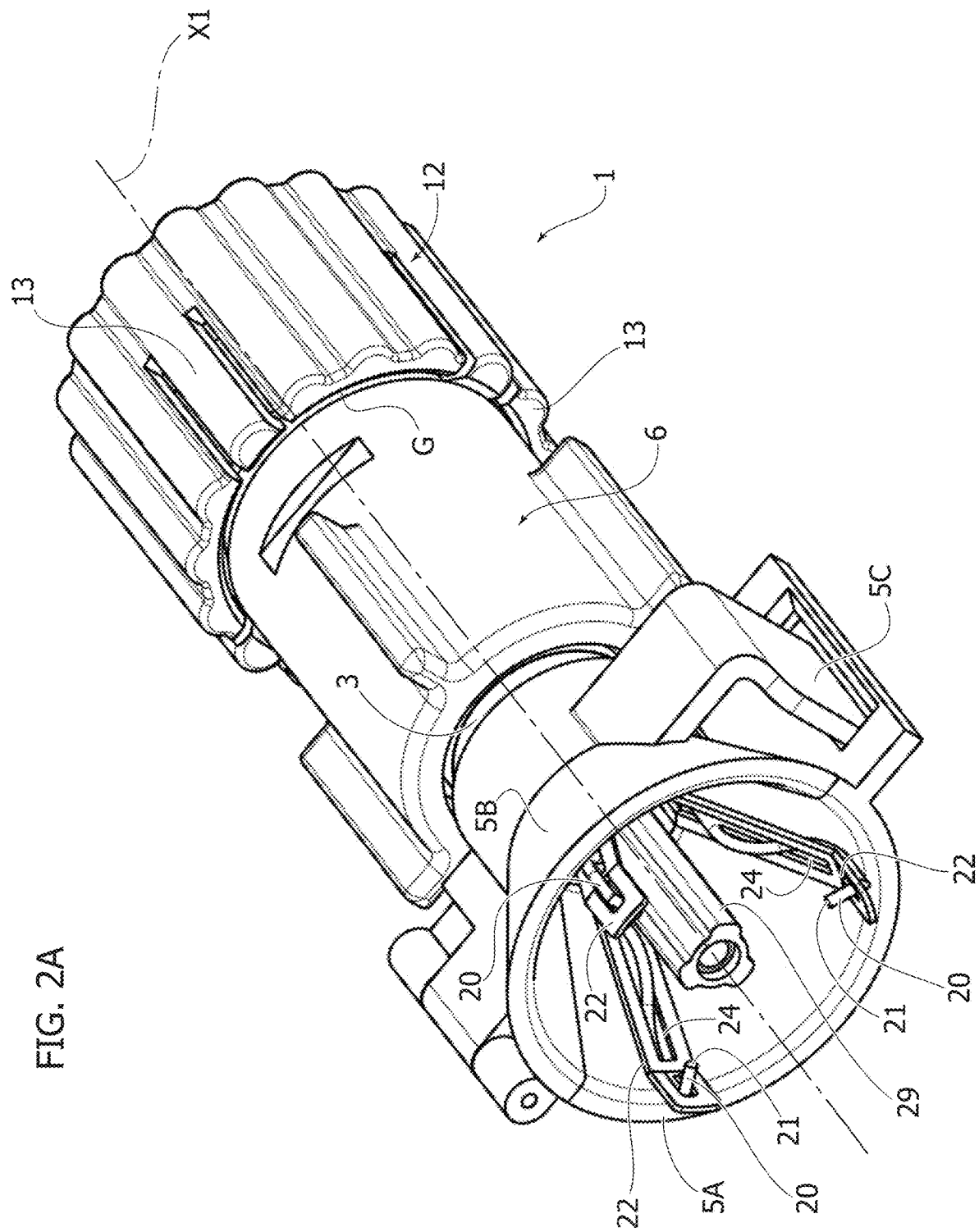
FIG. 2A is a perspective view of a loading system extracted from the container, according to embodiments of the disclosure.
Figure 2B:
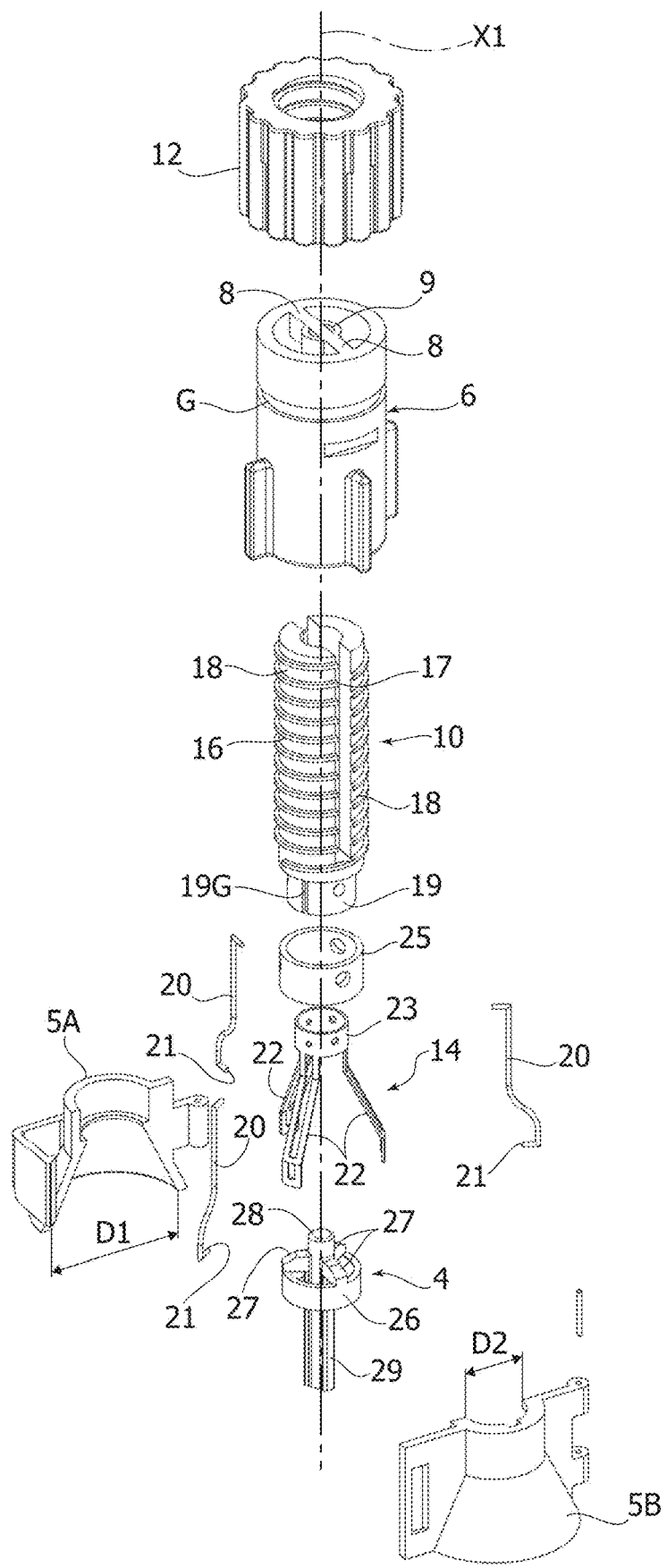
FIG. 2B is an exploded perspective view of a loading system, according to embodiments of the disclosure.
Figure 3A:
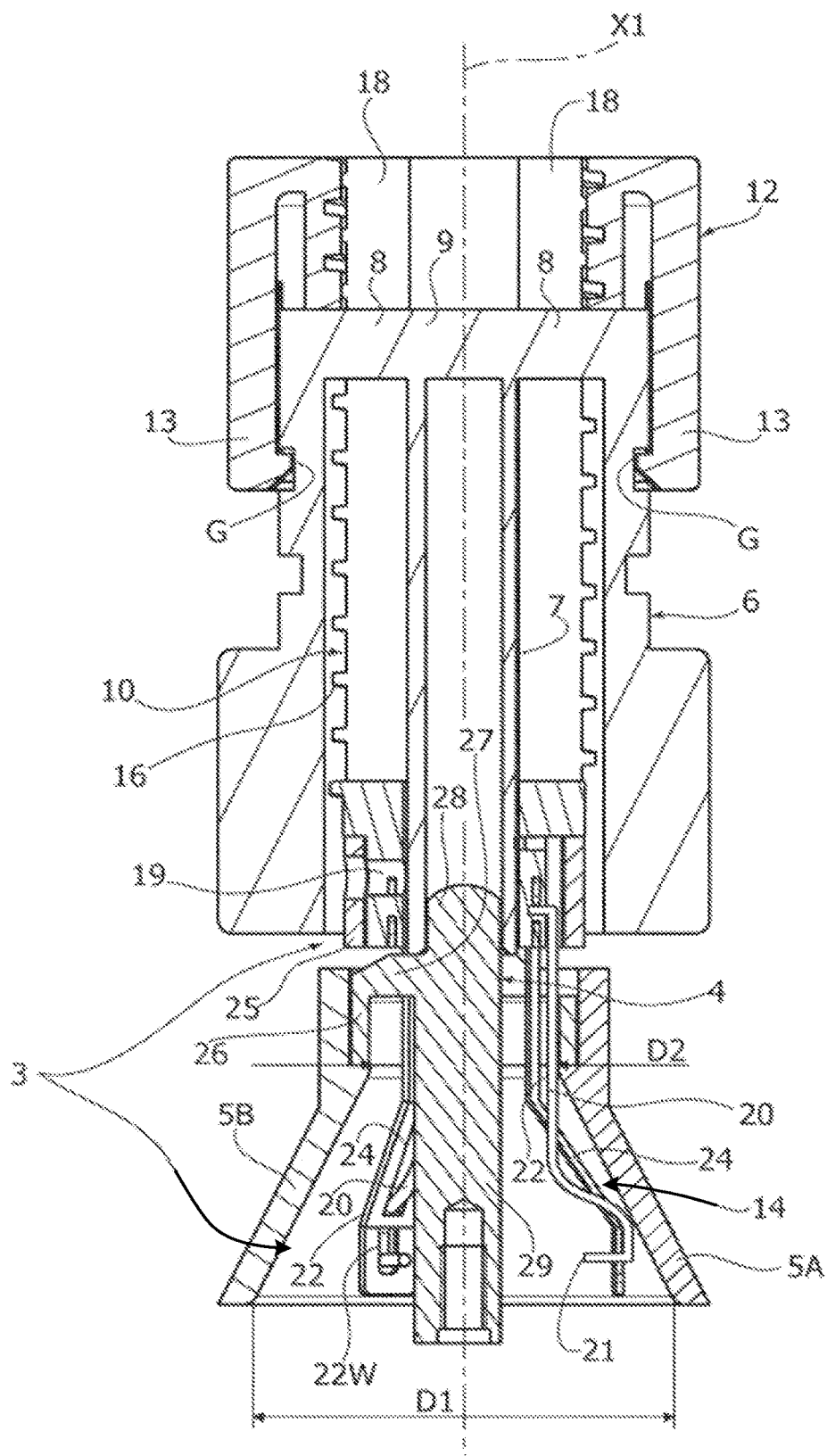
FIG. 3A is a longitudinal sectional view of the loading system, according to embodiments of the disclosure.
Figure 3B:
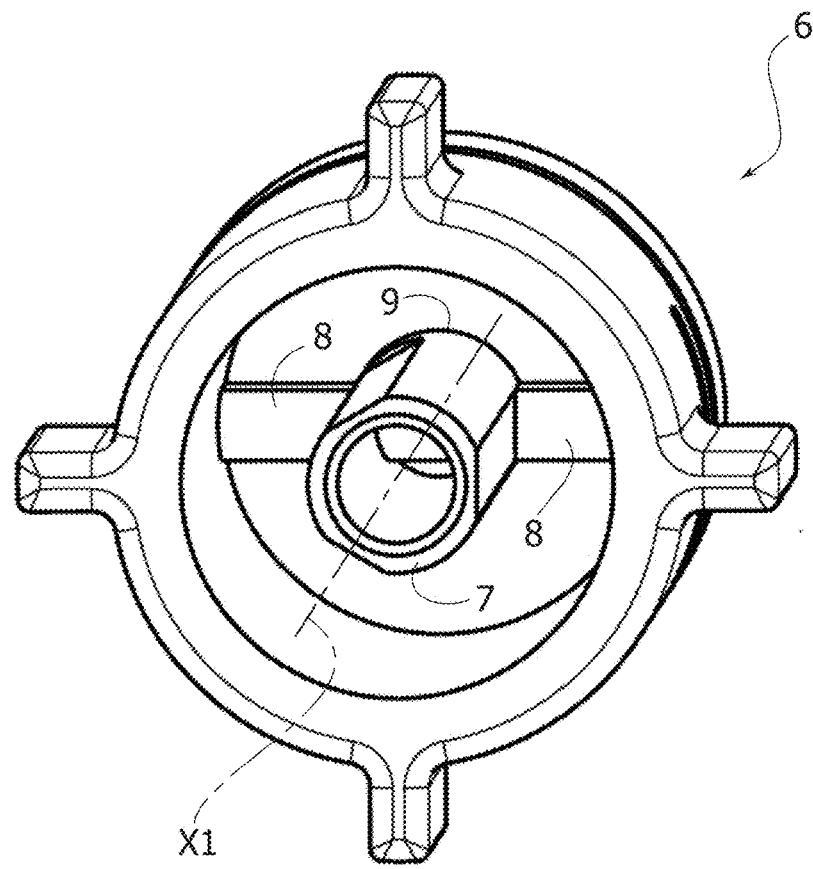
FIGS. 3B-3E are individual perspective views of single components or sub assemblies of the loading system, according to embodiments of the disclosure.

With reference to FIGS. 2B and 3A, in some embodiments, the loading system 1 includes a tubular member 6 which may define at least partly an outer shell for the gripper (or part thereof), as well as an attachment for a drive member of the gripper. The tubular member 6 is axially fixed relative to the gripper, and the gripper axially moves relative thereto.

The tubular member 6 can include a holder 7 that extends longitudinally along the axis X1 and coaxially thereto. The holder 7 is configured as a coupling seat for the first receiver 4. In some embodiments, such as shown in the figures, the holder 7 is a tubular member surrounded by the tubular member 6 that is suspended within the tubular member 6 by bridging formations 8 radially extending from a hub 9 coaxial to the axis X1. In some embodiments, a single bridging formation extending across the inner walls of the tubular member is provided, without the hub 9.

In embodiments, the gripper 3 includes a stud 10 (FIGS. 3A and 3C) encased by the tubular member 6 and a gripping portion 14 at one end of the stud 10. In the first axial position shown in FIG. 3A, the gripping portion 14 is arranged essentially at an axial location corresponding to the first funnel shaped element 5.

In embodiments, a drive member 12 engages the stud 10 to provide an axial displacement thereof upon operation of the drive member. In some embodiments, the drive member 12 is a rotary knob that engages the tubular member 6 at one end thereof opposite the end at which the gripping portion is arranged. Engagement may occur, as shown in FIG. 3A, by way of engagement of resilient formations 13—cantilevered to the main body of the rotary knob 12—into an annular groove G provided on the outer surface of the tubular member 6.

In embodiments, the rotary knob 12 includes an inner thread 15 that engages an outer thread 16 on the outer surface of the stud, so that a rotary operation of the rotary knob results in an axial motion of the stud, and the gripper as a whole, along the axis X1.

Alternatively, in some embodiments, another sort of cam mechanism may be provided between the drive member 12 and the gripper 3, for example a cam-pin engagement with the cam track provided on either of the drive member 12 and the stud 10, and the pin(s)/cam follower(s) provided on the other of the two.

Figure 3C:
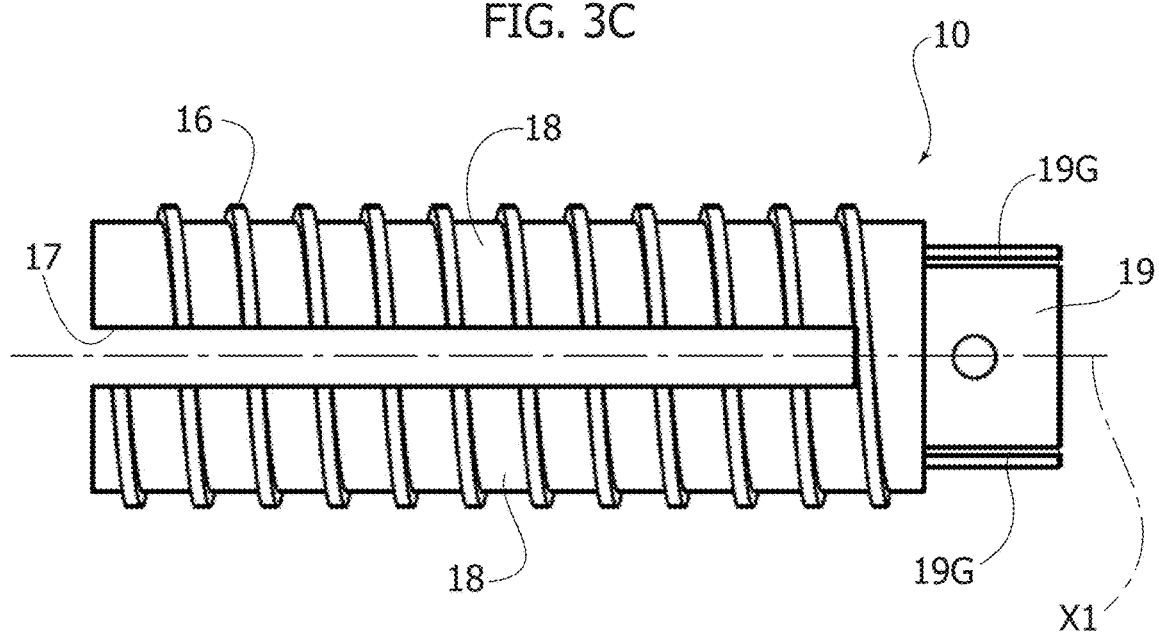

With reference to FIGS. 3A and 3C, in embodiments such as that depicted in the figures, the stud 10 is a hollow stud and includes an axial slot 17 that separates two semi-cylindrical axial portions 18 that may carry the thread 16 on the outer surface thereof (or the cam track/cam follower where appropriate). The axial slot 17 ends at an annular portion 19 wherein the two axial extensions 18 merge.

This design of the stud 10 allows the compenetration between the same and the holder 7 when the gripper 3 is inserted axially into the tubular member 6. Specifically, the hollow stud 10 is slidably fitted around the holder 7, thereby accommodating the same therein and between the axial extensions 18, while the axial slot 17 accommodates the bridging formations (or in general a bridge member) connecting the holder 7 to the tubular member 6.

Figure 3D:
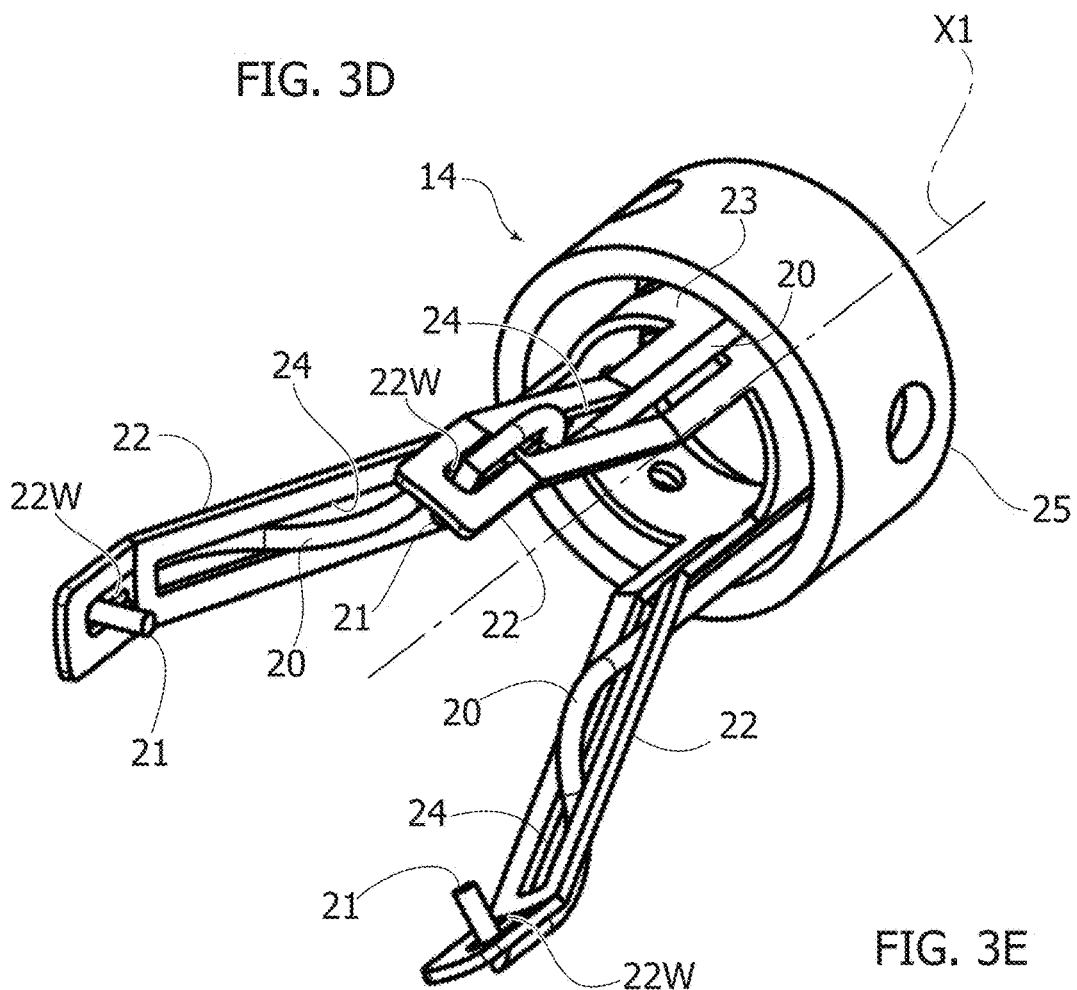

With reference to FIG. 3D, in embodiments such as per the figure the gripping portion 14 includes a plurality of resilient finger members 20 in a number that may depend on specific features of the heart valve prosthesis 2 that is coupled to the gripping portion. In some embodiments, which are suitable for engagement of an aortic valve prosthesis such as that visible in the subsequent FIG. 4A, the resilient fingers 20 are in the number of three, spaced 120 degrees apart. Each of the fingers 20 is radially displaceable from a radially divaricated condition (visible in FIG. 3A and in FIG. 3D) to a radially collapsed condition upon an axial displacement of the gripper 3 relative to the first funnel shaped element 5 from the first axial position to the second axial position. The resilient fingers 20 engage the heart valve prosthesis 2 radially outwardly of the same, and to this end they may be provided with inwardly pointing gripping ends 21. In some embodiments, as visible in figures, the fingers 20 are provided as separate wire like members that engage corresponding axial seats 19G on the annular portion 19 of the stud 10. In other embodiments, the fingers 20 come in one piece, for example as wire like extension from a common ring that is snap fit or otherwise engaged into a seat on the stud 10. Either way, in embodiments, the fingers 20 are mounted so to be cantilevered relative to the stud 10, so to exploit the inherent resiliency thereof to make for a return motion to the radially divaricated condition. In other embodiments, the resiliency of the fingers may be provided by a bias mechanism such as leaf springs or a rolled leaf springs cooperating with the fingers (which may be hinged instead of cantilevered).

In embodiments, each resilient finger 20 is associated to a guide blade 22, each guide blade being provided as an extension stemming from a ring member 23 which is fastened to the stud 10, particularly to the annular portion 19.

The guide blades 22 are positioned with the ring member 23 radially inwardly of the resilient finger set, and each include a longitudinal through slot 24 configured to accommodate the respective resilient finger 20 during a displacement of the same from the radially divaricated to the radially collapsed condition, thereby keeping the same aligned along a longitudinal direction. In embodiments, each resilient finger 20 runs axially parallel to the slot 24 and outside thereof, then bends radially outwardly to divert from axial orientation, further bends radially inwardly to regain axial orientation, then bends again—in one embodiment approximately 90 degrees—radially inwardly to weave through the tip of the respective blade 22, particularly through an opening 22W at the tip of the blade 22, to protrude radially inwardly of the gripping portion 14 and of the blades 22.

This arrangement is generally achieved when the gripping portion 14 is assembled into the loading system 1, with a certain degree of radial constraint applied to the fingers 20.

In embodiments, the resilient fingers 20 are shaped so to exhibit, when radially unconstrained, a generally flared pattern wherein no engagement is provided between the tips 21 and the openings 22W. This is intended to facilitate attachment of the valve when pre-assembling the loading system upon manufacturing thereof, as well as—as will be detailed further on—to allow smooth release of the loaded valve when needed.

It may also be noted that in embodiments wherein the axial length prior to the first bend away from the axis is such as to allow the finger 20 to enter the slot 24 from the outside thereof (see, purely for exemplary purposes, FIG. 3A), only to exit the slot 24 when bending radially outwardly as described above.

Due to the fingers 20 generally having—in embodiments—a marked elongation compared to the cross section thereof, a risk exists that the same get eventually twisted or otherwise distorted when subject to a radial collapsing action, which is undesired. Therefore, the slots 24 are configured to accommodate the fingers 20 by a variable extent during radial contraction, so that the resilient fingers will contact two separate axial locations within the slot 24 to counter distortion or other twisting phenomena.

In embodiments, a locking ring 25 may be provided surrounding the ring member 23, to secure connect the resilient fingers 20 to the blades 22. The locking ring 25 is then fitted, e.g. force fitted, onto the annular portion 19, wherein force fitting also involves sandwiching the resilient fingers and the ring member (in this order from outside in) between the locking ring 25 and the annular portion 19.

Figure 3E:
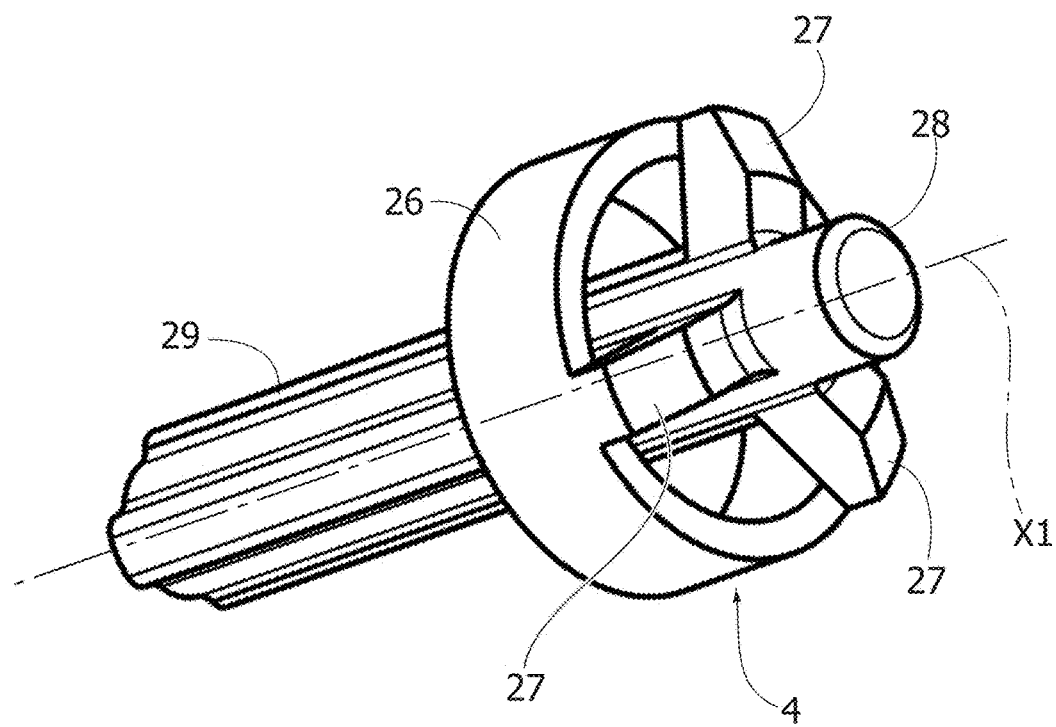

With reference to FIG. 3E, the first receiver 4 includes ring 26 connected by spoke like formations 27 to an axially protruding hub 28, wherein the hub 28 is configured to mate with the holder 7 at an end thereof opposite to that where the hub 9 is located. Additionally, the receiver 4 may be provided with an axial extension 29 of the hub 28, which extends to an opposite direction relative to the protrusion of the hub 28, and that is configured for mating with an additional component of the loading system 1 that, in some embodiments, is used to provide a cooperative loading of the heart valve prosthesis 2.

The spoke like formations 27 are provided in the same number as that of the fingers 20, as the spoke like formations 27 allow a compenetration between the gripping portion 14 and the receiver 4 as visible in FIG. 3A. Specifically, in embodiments, each finger 20-blade 22 pair traverses the receiver 4 between two adjacent spoke like formations 27.

Owing to this arrangement, the gripping portion 14 is enabled to axially displace relative to the receiver 4 along the axis X1.

Referring again to FIGS. 2A and 3A the first funnel shaped element 5 is removably coupled to the loading system 1, and specifically it is removably coupled to the receiver 4, in turn mated to the holder 7. In embodiments, removable coupling is provided by the funnel shaped element 5 comprising two halves 5A, 5C hinged to one another and locked into a funnel shape by a snap fit closure 5C.

Figure 4A:
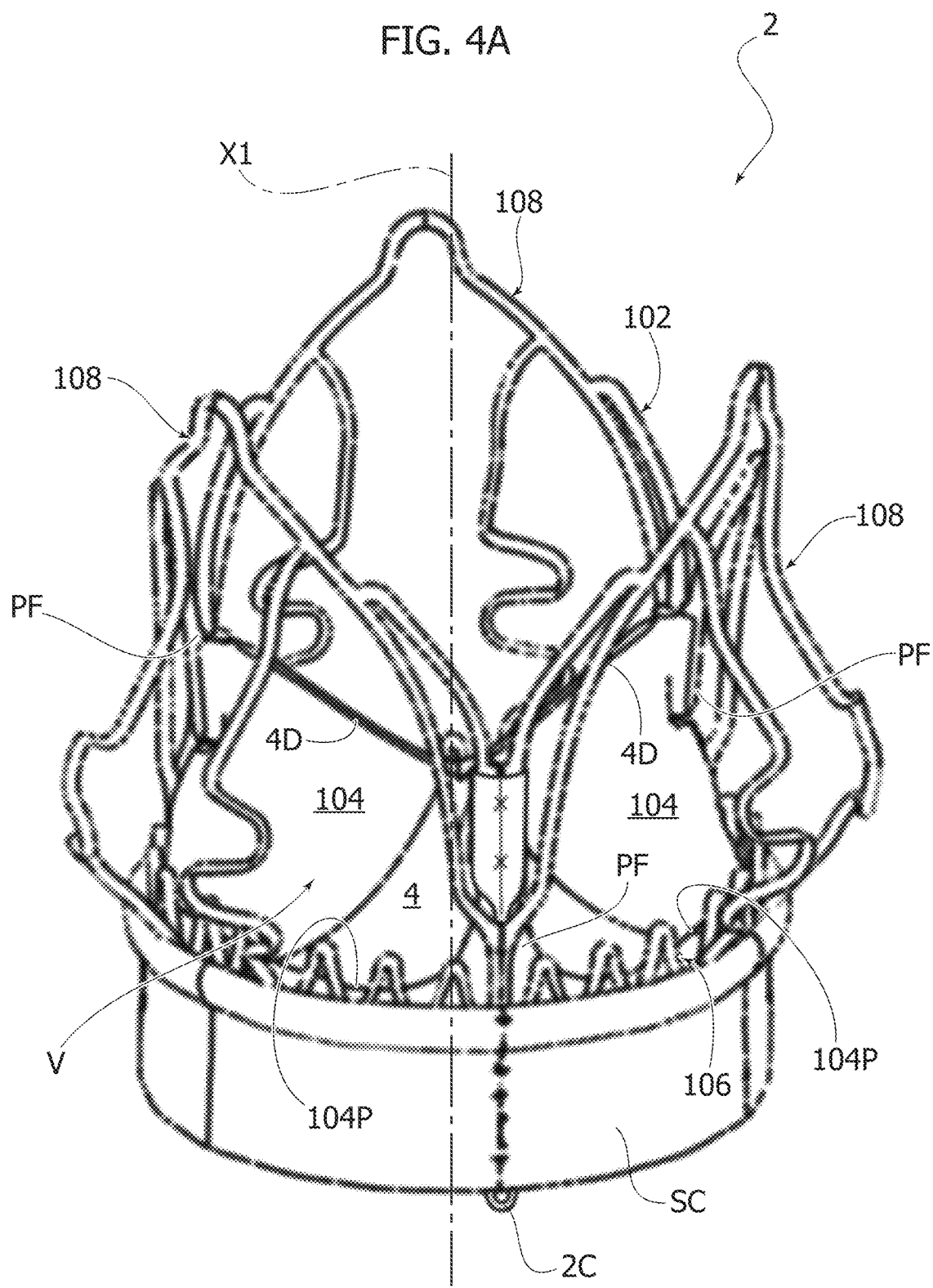
FIG. 4A is a perspective view of an exemplary heart valve prosthesis in the loading system, according to embodiments of the disclosure.
Figure 4B:
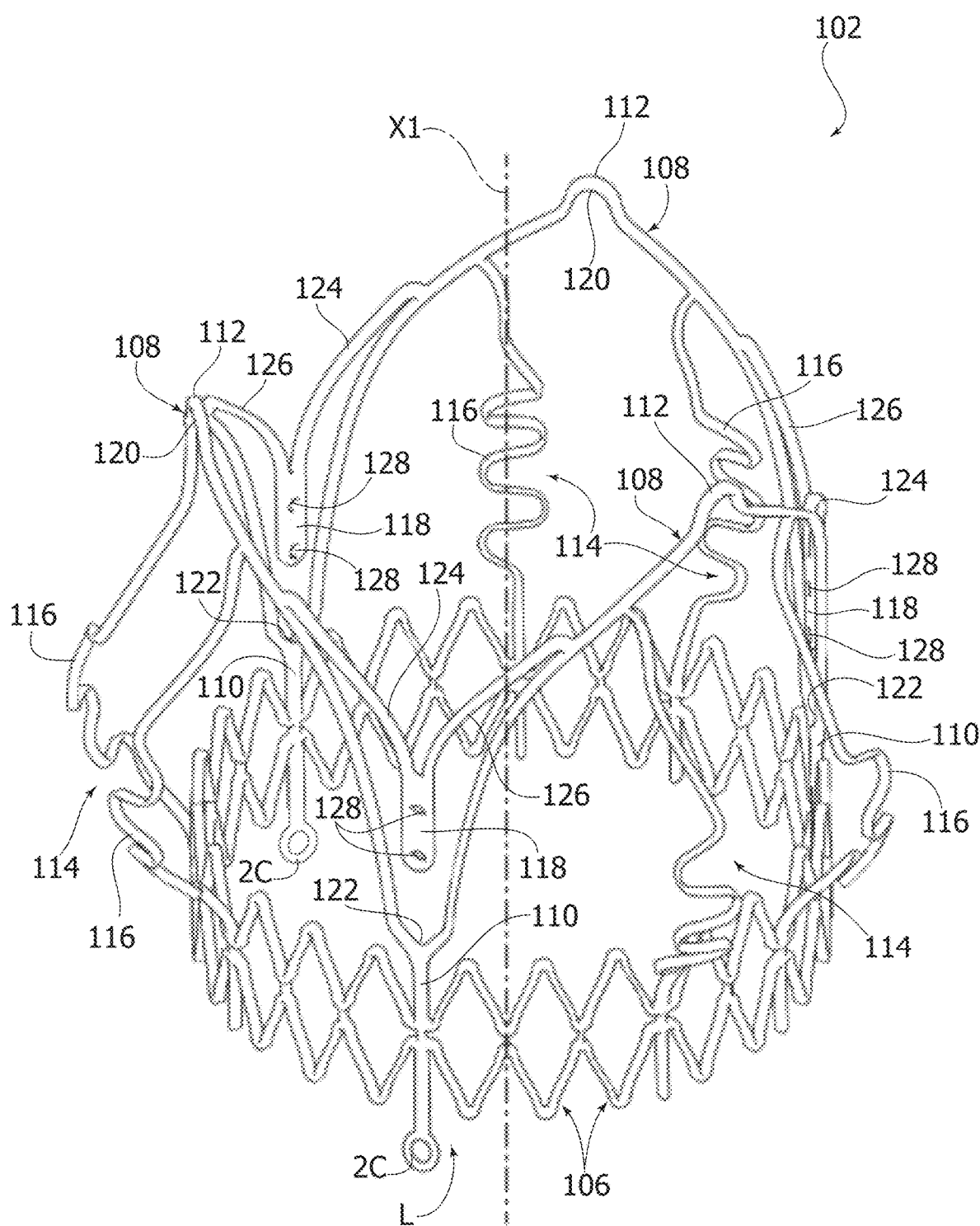
FIG. 4B is a perspective view of the armature thereof, according to embodiments of the disclosure.

With reference to FIGS. 4A and 4B, the prosthesis 2 and the armature thereof are respectively depicted therein. The heart valve prosthesis 2 includes an armature 102 for anchorage of the valve prosthesis at an implantation site. The armature 102 defines a lumen for the passage of the blood flow and has a longitudinal axis X2.

The prosthesis 2 also includes a set of prosthetic valve leaflets 104 supported by the armature 102 and configured to move, under the action of blood flow (which has a main flow direction roughly corresponding to that of the axis X1):

in a radially divaricated condition to enable the flow of blood through the lumen in a first direction, and in a radially contracted condition, in which the valve leaflets 104 co-operate with one another and block the flow of blood through the prosthesis 1 in the direction opposite the first direction. This is commonly referred to as leaflet coaptation.

The prosthetic leaflets 104 may be in any number compatible with operation as replacement heart valve.

In some embodiments, the set includes a pair of leaflets. In some embodiments, such as that shown in the figures, the set includes three prosthetic valve leaflets 104 (e.g. for an aortic valve prosthesis). In some embodiments, the set may include four leaflets 104.

The armature 102 includes an annular part 106, and a pattern of arched struts 108 carried by the annular part 106. The annular part 106 has a structure which can expand from a radially contracted condition, associated to delivery of the prosthesis to implantation site, to a radially expanded condition wherein the prosthesis is withheld at the implantation site. In embodiments, the annular part may have a mesh structure including an annular pattern of multiple strut clusters (cells) having polygonal shape (hexagonal, rhomboidal, etc.).

In embodiments, the annular part is covered by a cuff such as the sealing cuff SC to provide sealing at the implantation site, the cuff being arranged outside of the lumen of the armature 102. The cuff may be sewn or stitched to the annular part 106. The annular part 106 with the sewing cuff attached thereto provides an inflow portion of the heart valve prosthesis 2.

As described, depending on the technique used to manufacture the valvular sleeve, wherein the cuff SC may be integral with the set of prosthetic valve leaflets 104.

The annular part 106, and particularly the sealing cuff SC are provided with coupling elements 2C intended to be engaged by the resilient fingers 20 (they may be engaged by the radially protruding tips 21, where provided) the way exemplified in FIG. 3A. In some embodiments, the coupling elements 2C may be provided as loop elements attached to the sealing cuff, and preferably provided by a thread or yarn that is weaved through the sealing cuff SC. In some embodiments, the coupling elements 2C may be provided integrally with the armature 102 circumferentially aligned with the support posts 118, albeit axially past the annular part 106 at the inflow portion (i.e. the coupling elements 2C protrude axially away from the annular part 106) as visible in FIG. 4B.

The pattern of arched struts 108 includes proximal ends 110 connected to the annular part 106, and distal ends 112 spaced axially from the proximal ends 110 and arranged at an end of the armature 102 opposite the annular part 106. In embodiments, the distal ends 112 coincide with distal ends of the armature 102, and in some embodiments where the distal end of the armature 102 coincides with a distal end of the prosthesis 100 as a whole, the distal ends 112 coincide with a distal end of the prosthesis as well.

The armature 102 further includes:

a plurality of sets 114 of anchoring formations 116 configured to protrude radially outwardly of the annular part 106, each set 114 being supported by at least one of the annular part 106 and a corresponding arched strut 108; and a plurality of support posts 118, each supported by adjacent arched struts 108, wherein the sets 114 of anchoring formations 116 alternate with the support posts 118 around the longitudinal axis X1. In various embodiments the support posts 118 are cantilevered to adjacent arched struts 108 and are configured as fixing locations for the prosthetic valve, specifically for the pleat formations PF at the commissural points of the valve.

Each arched strut 108 extends from a first proximal end 110, to a distal end 112, then to a second proximal end 110 in a valley-peak-valley sequence, wherein valleys are located at the proximal ends 110, and peaks are located at the distal ends 112. In embodiments the pattern of arched struts includes three adjacent and preferably identical arched struts 108 (such as in the figures).

The pattern of arched struts 108 includes distal portions 120 located at the distal ends 112, and inter-strut portions 122 located at the proximal ends 110.

The distal portions 120 may be shaped to provide a marked local variation in the shape of the strut, for example by exhibiting a C-shape as shown in the figure. The distal portions 120 provide coupling locations for other devices such as a valve holder or a hub of a carrier portion of a delivery catheter. In other embodiments, the distal portions 120 are provided as closed-loop structures such as eyes or eyelets. The pattern of arched struts 108, and particularly the distal ends with the distal portion 120 thereof provide an outflow portion of the prosthesis 2.

In embodiments, the inter-strut portions 122 are essentially V-shaped and are defined by the roots of the adjacent arched struts departing from the same proximal end 110. In some embodiments, the inter strut portions 122 may exhibit a Y-shape such as, for instance, that shown in the figure wherein each inter-strut portion 122 extends through the mesh of the annular part 106. Alternatively, they may exhibit a U-shape. In embodiments, the mesh of the annular part 106 is provided as a sequence of rhomboidal strut clusters (cells) sequentially connected to each other at endpoints of a diagonal line (typically the shortest diagonal) and exhibiting accordingly an identical circular pattern of free ends on opposite sides of a circumference extending through the sequence of the connection points. The Y-shaped inter-strut portion 122 is thus integrally formed at a selected connection point between two adjacent rhomboidal strut clusters, and, in some embodiments, extends no further than the proximal end of the armature 102.

The support posts 118 are angularly arranged at an inter-strut location, i.e. a circumferential location arranged at an area where an inter-strut portion 122 (as well as—accordingly—a proximal end 110 shared by two adjacent arched struts 108) is provided. The support posts are provided as cantilevered to both the adjacent arched struts 8 intervening at an inter-strut portion 122 via a first and a second cantilever struts 124, 126, each connected to a corresponding one of said adjacent arched struts 8 as shown in the figures. The cantilever struts 124, 126 merge into each corresponding post 118 starting from locations on respective arched strut 108 approximately halfway through the portion of the arched strut 108 extending from a proximal end 110 to a distal end 112. The connection points at which the Y-shaped inter-strut portion 122 is formed may be chosen so that the same portions are evenly spaced (angular-wise) around the axis X1. The same applies to the support posts 118, which may be arranged to be evenly spaced (angular-wise) around the axis X1.

In embodiments, the armature 102 comprises three arched struts 108, three posts 118 spaced 120° around the axis X1, and three sets 114, so that the sequence around the axis X1 is post 118—set 114—post 118—set 114—post 118—set 114 (in this sense, even the struts 108 and the sets 114 do follow a 120 degree-like distribution). In embodiments, the three sets 114 include each a pair of anchoring formations 116, wherein each set 114 (and accordingly each anchoring formation 116) extends bridge-wise between the annular part 106 and the corresponding arched strut 108.

Further details of the prosthesis 2 are disclosed in PCT application no. PCT/IB2018/053640 filed on even date herewith and in the name of the same Applicant, the disclosure of which is hereby incorporated by reference herein.

With reference to FIG. 5A, reference number 30 designates a delivery instrument that in embodiments forms part of the loading system 1 of this disclosure.

The delivery instrument 30 is configured to be used with the prosthesis 2 or in general it is an instrument configured to be used with any prosthesis intended to be loaded by way of the loading system 1.

In embodiments as shown herein, the delivery instrument including a shaft 31, a hub 32 carried by the shaft 31, and a second receiver 33 which is axially slidable relative to the hub 32 from a third axial position III to a fourth axial position IV. In embodiments, the second receiver 33 is a sheath member slidable over the hub 32, and exhibiting a variable degree of overlap relative thereto.

To this end, the delivery instrument 30, in embodiments, includes a rotary drive member 34 that is configured to impart a linear axial motion to the receiver 33 along the axis X1. In other embodiments, the rotary drive member 34 may be replaced by a linear drive member.

A handle 35 may be conveniently provided at one end of the shaft 31 to allow for easier manipulation of the instrument 30. In some embodiments, the rotary drive member 34 (or linear drive member where applicable) is provided on the handle 35.

Pursuant to aspects of this disclosure, the hub 32 of the delivery instrument 30 is configured for coupling with the first receiver 4: to this end, a coupling member 36 (e.g. a threaded member or else a mating pin) may be provided at a free end of the hub 32 to dock with the receiver 4, particularly with the axial extension 29 of the hub 28, and secure thereto.

In embodiments, such as those shown herein, the second receiver 33 includes a second funnel shaped element 37 coupled thereto, the second funnel shaped element 37 having a third diameter D3 and a fourth diameter D4, the fourth diameter D4 being smaller than the third diameter D3 and being axially closer to the second receiver 33 than the third diameter D3 (FIG. 5B). The funnel shaped element 37 is detachably coupled to the receiver 33, in a way similar to the funnel shaped element 4. For example, the funnel shaped element 37 may be provided as including two halves that can be separated or opened upon undoing a locking feature or mechanism thereof, or else the funnel shaped element 37 may be provided as a one-piece element that interference fits with the receiver 33, while allowing for a detachment from the same.

With reference to FIGS. 6A to 10, as well as cross support from FIGS. 1 to 5B, operation of the loading system 1 in embodiments disclosed herein will now be detailed.

Figure 6A:
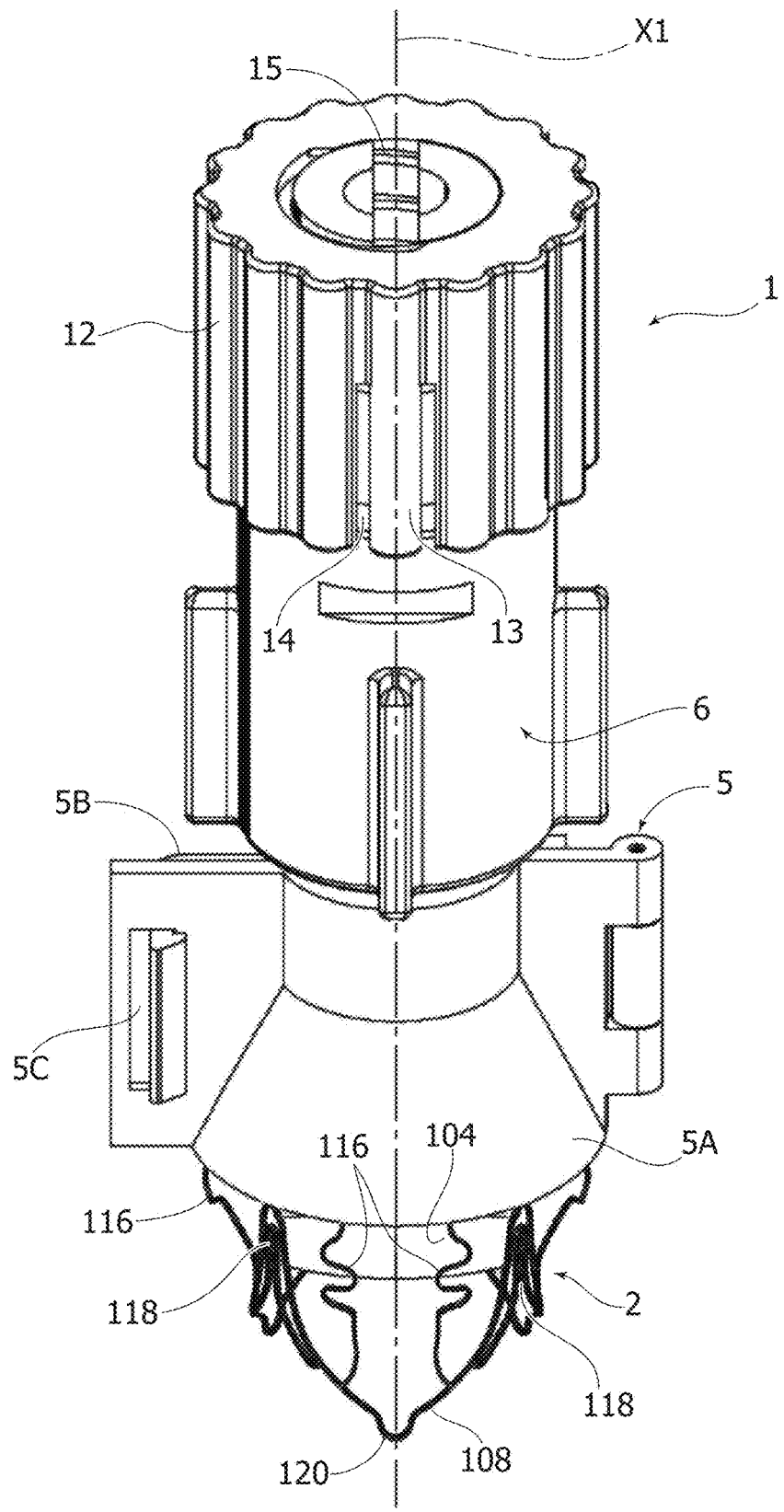
FIGS. 6A to 10 illustrate an operating sequence of the loading system, according to embodiments of the disclosure, with FIG. 6B illustrating a functional detail applying to FIG. 6A, according to embodiments of the disclosure.

With reference to FIG. 6A, in embodiments, the loading system 1 comes as a pre-mounted kit including the funnel shaped element 5, and wherein the gripper 3 is in the first axial position I along the axis X1 and engages the heart valve prosthesis 2 essentially in a radially unconstrained condition due to the engagement of the coupling elements 2C. The coupling element 2C are traversed by the resilient fingers 20, and especially by the tips 21 thereof, and are accordingly each secured between a finger 20 and the respective blade 22 the finger 20 runs through.

The heart valve prosthesis, in some embodiments, is preferentially mounted to be slightly pre-loaded axial wise (see FIGS. 1 and 6A), for example by having the inflow portion with the annular part 106 and the sealing cuff SC abutting on the funnel shaped element 5, that is likewise pre-mounted on the loading system 1. The condition referred to corresponds to that visible in FIG. 3A with the heart valve prosthesis 2 in phantom line. In embodiments, the portion of the prosthesis 2 disclosed in FIGS. 4A and 4B that is coupled to the gripper 3 is an inflow portion associated to annular part 106 of the armature 102 (at the sealing cuff SC), which includes the coupling elements 2C.

In some embodiments, the loading system 1 with the prosthesis 2 pre-mounted therein may be provided stored in a jar J (FIG. 1) filled with a sterile preservation solution and closed by a cap.

A centering flange or disc DS may additionally be fitted onto the tubular member 6 to provide radial centering and axial support within the jar J.

Figure 6B:
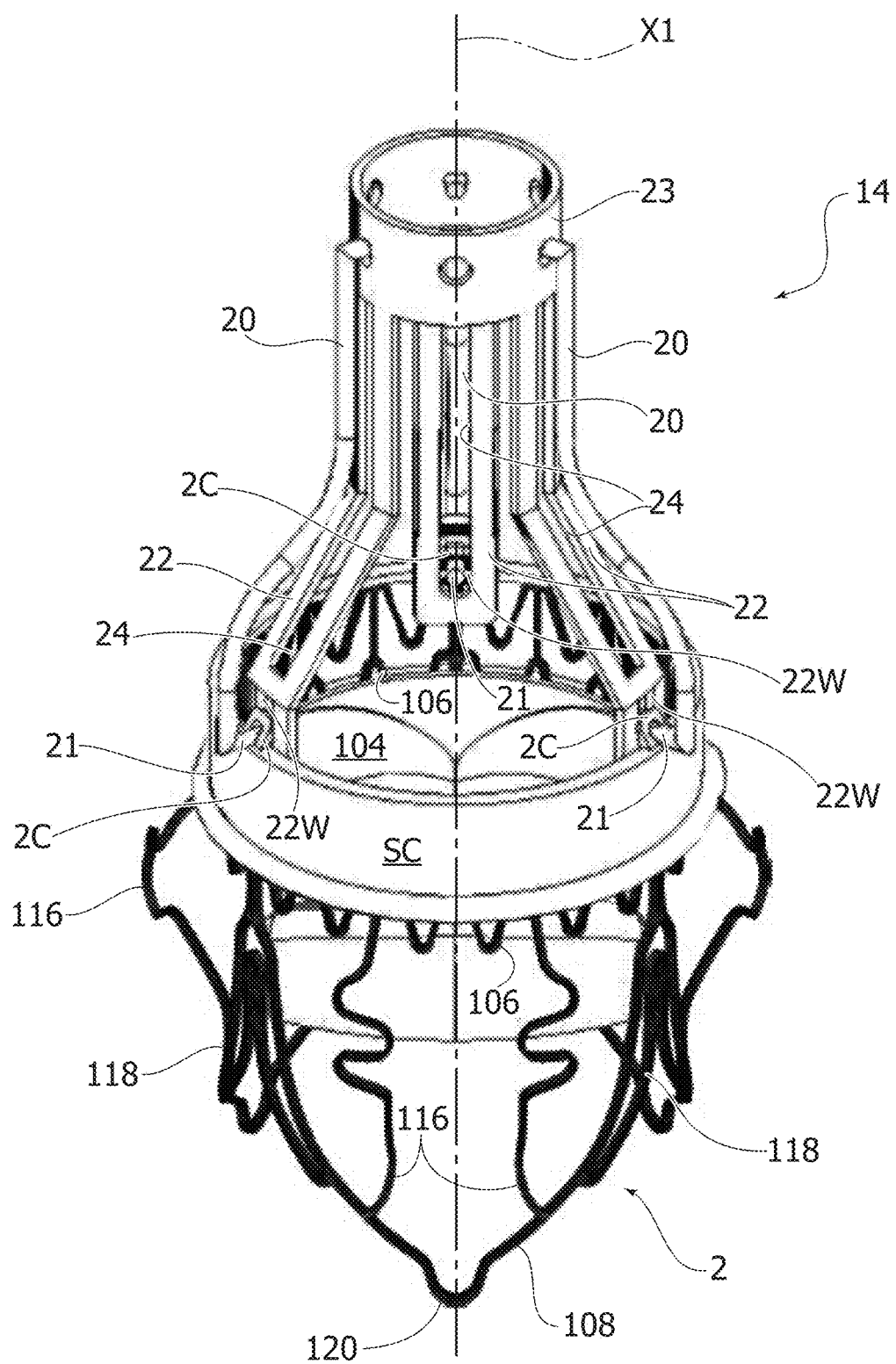

Once the loading system is extracted from the jar J—FIG. 6A—or anyway grabbed by the practitioner, loading of the heart valve prosthesis 2 may begin. In embodiments, this is done by operating the drive member 12, for example—in case of a rotary drive member as shown in the figures—by rotating the same around the axis X1 to provide an axial displacement of the gripper 3 from the first axial position I to the second axial position II. FIG. 6B illustrate a detail of the gripping portion holding the valve prosthesis 2 just out form the jar J, with the resilient fingers 20 engaging the coupling elements 2C.

Purely by reference, the description that follows will be rendered assuming clockwise rotation as the driving action that brings the gripper 3 from the first to the second axial position, and accordingly counterclockwise rotation as the action that brings the gripper 3 from the second axial position to the first axial position. Clearly, this is purely a disclosure assumption: the loading systems can operate whatever association is made, i.e. it operates just the same with clockwise and counterclockwise directions swapped.

Rotation of the drive member 12 in the clockwise direction translates the stud 10 and the gripping portion 14 axially towards the second position II, while the receiver 4 remains steady and mated to the holder 7. This creates a relative axial motion between the heart valve prosthesis and the funnel shaped element 5, and specifically the heart valve prosthesis 2 is dragged axially along the axis X1 from the first axial position I to the second axial position II, thereby negotiating the disparate diameters from D1 to D2. Negotiating the disparate diameters from D1 to D2 accordingly results in a radial contraction of the armature 102 of the heart valve prosthesis 2.

Operation of the drive member 12 proceeds until the radially collapsed portion of the armature of the heart valve prosthesis 2, which in the sequence depicted in the figures is the inflow portion associated to the sealing cuff SC whereat the coupling elements 2C are provided, slides into the receiver 4, thereby getting loaded into the annular portion 26 of the same.

In this regard, the compenetration between the fingers 20 and the spoke like formations 27 also allows for a relative motion between the groups of fingers 20 and related blades 22 and the receiver 4, also accommodating the radial collapse of the fingers 20. In fact, during transition from the first axial position I to the second axial position II the fingers 20 are radially collapsed as well due to the interaction with the funnel shaped element 5. The provision of guide blades 22—that move integrally with the gripper 3—prevents undesired twists or rotations of the fingers 20, as described.

As visible in FIG. 3A, in embodiments, the diameter D2 may be conveniently provided as identical or anyway closely matching the inner diameter of the receiver 4, particularly the inner diameter of the annular portion 26. This facilitates the transition of the (inflow) portion of the heart valve prosthesis 2 from the funnel shaped element 5 to the receiver 4, thereby allowing for a smoother loading of the same into the receiver 4.

Figure 7:
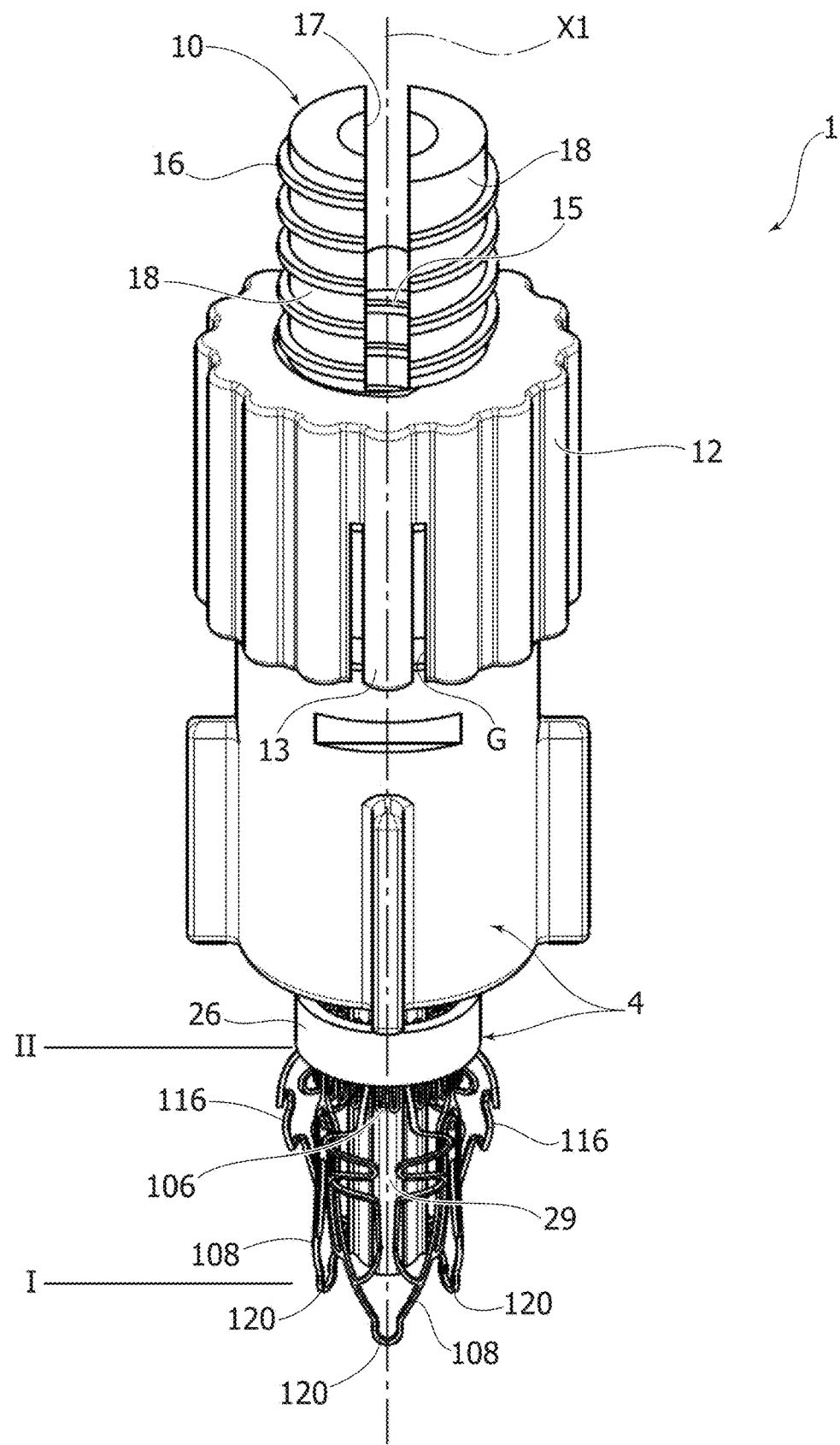

The resulting condition, reached at the second axial position II, is shown in FIG. 7. Specifically, following loading of the inflow portion of the heart valve prosthesis 2 into the receiver, the funnel shaped element 5 is detached from the loading system, for example by opening the two halves 5A, 5B.

In the above regard, it is significant to note that when the gripper reaches the second axial position II, the resilient fingers 20 are located axially outside of the receiver 4. This is clearly visible in FIG. 7 in that it is the annular part 106 (with the sealing cuff on the outside thereof) that is sitting into the receiver 4, surrounded and held collapsed by the annular member 26.

In other words, following displacement of the fingers 20 through the inter-spoke areas of the receiver 4 (i.e. the areas between adjacent spoke like formations 27), the fingers 20 end up with sitting past the annular portion 26 (towards position II) with the coupling elements 2C still engaged thereby. The prosthesis 2 cannot migrate any further owing to the shape of the receiver 4, i.e. the very spoke like formations 27 that allow the fingers 20 to move past the receiver provide an axial stop to the prosthesis 2. In embodiments, the final position may feature the fingers 20 engaged with slightly tensioned coupling formations 2C that protrude axially away from the annular portion 26 while the inflow portion of the prosthesis 2 is firmly held into (and by) the receiver 4. In this condition, the fingers 20 are actually held in a radially collapsed condition by the inner walls of the tubular member 6 as the same fingers end up with being actually accommodated therein when the stud 10 is axially retracted to bring the gripper 3 in the second axial position II.

Figure 8:
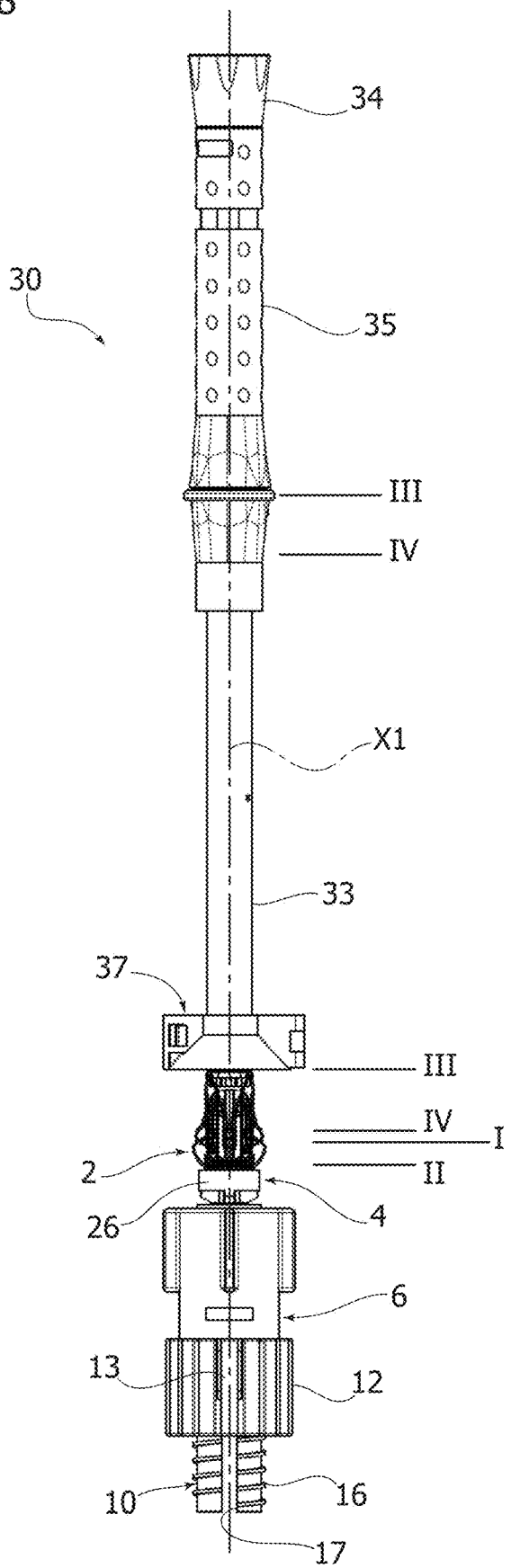

Next—FIG. 8—the delivery instrument 30 with the funnel shaped element 37 pre-mounted thereon is mated to the receiver 4, which in embodiments may occur by engagement of the coupling extension 36 with the axial extension 29 of the receiver 4, for example by a threaded connection or a snap fit connection.

Mating is effected such that the third diameter D3 of the funnel shaped element 37 is presented with the heart valve prosthesis 2, still held by the gripper 3.

At this stage, the armature of the heart valve prosthesis 2 not constrained by the receiver, which in embodiments corresponds to the outflow portion at which the distal ends of the arched struts 108 are located, is still free from radial contraction.

When the funnel shaped member 37 is presented with the valve prosthesis 2, the distal ends of the arched struts 108 might be even slightly flared outwards due to the contraction of the inflow portion by the first receiver 4, while the outflow portion is substantially unconstrained in itself.

In embodiments as shown herein, loading of the outflow portion of the prosthesis 102 occurs at the delivery instrument 30, and specifically the outflow portion of the prosthesis 102 is intended to be loaded into the second receiver 33.

To accomplish this, in embodiments, an axial displacement of the second receiver 33 from the third axial position III to the fourth axial position IV is provided—either by way of the drive member 34 or by a direct axial displacement of the receiver 33—so that the second funnel shaped element 37 moves axially relative to the heart valve prosthesis 102.

In embodiments, the delivery instrument may envisage an override mechanism that allows for an axial displacement of the receiver 33 independently of the drive member 34 to provide for a fast advance of the receiver 33 towards the third axial position. An example of such an override mechanism can be found, e.g. in European Patent no. EP 2 250 975 B1 in the name of the same Applicant, which is hereby incorporated by reference herein. The advanced position of the receiver 33 achieved thanks to the override mechanism above may be maintained in embodiments by way of a spacer clip CL that fits between the (advanced) receiver 33 and the handle 35.

Figure 9:
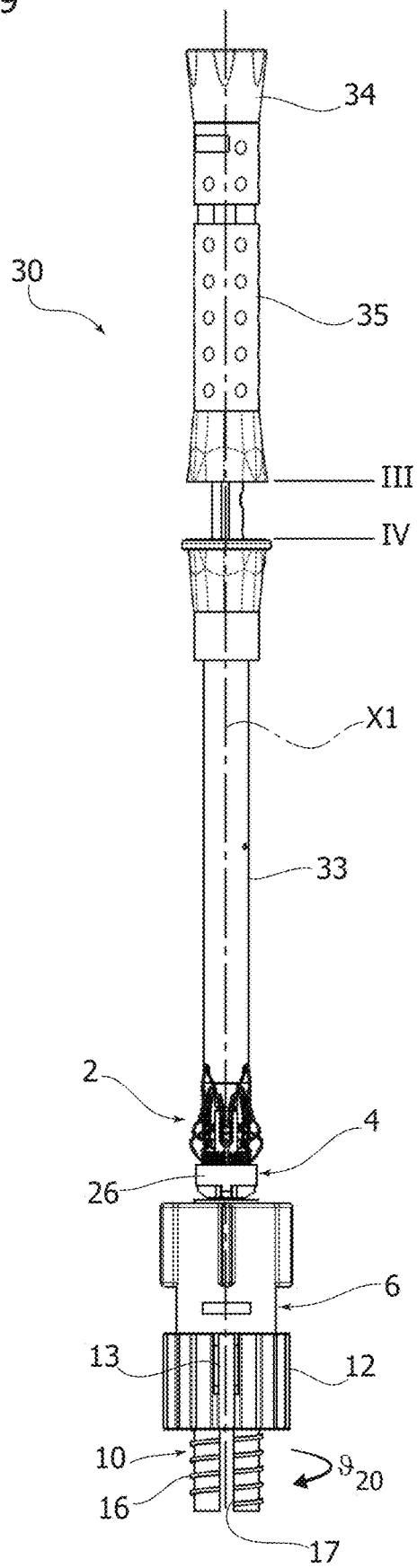

Accordingly, the outflow portion of the prosthesis 102 negotiates the disparate diameters from D3 to D4, that is, it negotiates a lumen narrowing from the third diameter D3 to the fourth diameter D4. Radial contraction of the distal ends of the arched struts 108—and the outflow portion too in the process—is therefore provided, so that the outflow portion comes to fit into the second receiver 33 in a radially contracted condition (FIG. 9)

Similar to the funnel shaped element 5, the funnel shaped element 37 may then be detached from the delivery instrument 30 (FIG. 9 already shows the loading system 1 with the funnel shaped member 37 detached) for example by opening the two halves thereof. This may be considered a preferred solution in that owing to the delivery instrument being mated to the receiver 4, axially removing the funnel shaped element 37 at this stage may turn out to hinder the subsequent stages of the loading method.

With reference again to FIG. 9, it may be noted therefore that once the two funnel shaped members are removed, the first one when the gripper is in the second axial position II, the second one when the second receiver is in the fourth axial position IV, the result is that of the first receiver 4 and the second receiver 33 providing deployment elements of the delivery instrument. More in detail, in embodiments, the first receiver 4 may provide an inflow deployment element intended to hold the inflow portion of the prosthesis 2 (here, essentially the annular portion 106 of the armature with the sealing cuff SC) in a radially contracted condition and release the same on site when later operated, while the second receiver 33 may provide an outflow deployment element intended to hold the outflow portion of the prosthesis 2 (here, essentially the distal end of the prosthesis at the distal end portions 120 of the arched struts 108) and release the same on site when later operated.

In order for the delivery instrument to be later used as indicated above, the receiver 4 is to be detached from the holder 7 while remaining mated to the hub 32. To do this, in embodiments, the gripper 3 is to be first released from the heart valve prosthesis 2.

This is achieved, in embodiments, by operating the drive member 12 counterclockwise, or more in general in a direction opposite to that which results in displacement of the gripper to the second axial position II. This operation of the drive member 12 advances the gripping portion 14 with the resilient fingers 20 axially towards position I, and ultimately away from the tubular member 6. While the fingers 20 gradually exit the tubular member 6, the radial contracting action exerted thereon by the tubular member is released as well (this, also by virtue of the flared pattern of the resilient fingers 20), thus allowing the same to get back to the radially divaricated condition they exhibit at the beginning of the loading operation, and even past that to a more divaricated arrangement which corresponds to the unconstrained condition mentioned in the foregoing. That is, the resilient fingers are allowed to expand back to an unconstrained condition wherein they also release engagement with the blades 22 at least at the openings 22W thereof, so that the prosthesis 2 is allowed to smoothly become free of the gripping portion 14.

The same release is not extended to the inflow portion of the heart valve prosthesis 2, as the same is kept radially contracted by the annular portion 26 of the receiver 4.

As the gripper 3 constrains the prosthesis 2 radially outwardly thereof via the fingers 20, the latter in turn do not have any stop or otherwise constraint feature that holds them in engagement with the coupling elements 2C when the fingers 20 are subject to a radially outward motion relative to the prosthesis 2.

Accordingly, while the prosthesis 2 remains within the receiver 4, the fingers 20 are biased back to/towards the divaricated condition which allows them to simply slip away from engagement with the coupling elements 2C in a radially outward direction (see rotation $\theta_{20}$ in FIG. 9), thereby releasing the inflow portion of the prosthesis 2 from the gripper 3.

Figure 10:
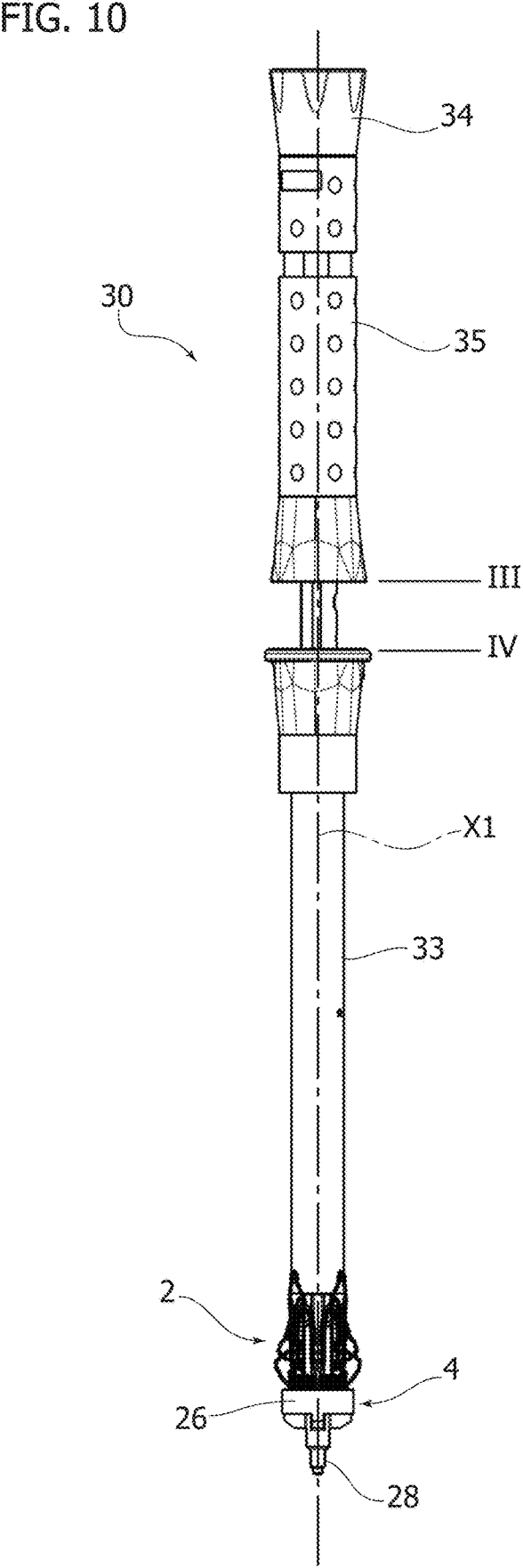

Next, the receiver 4 may be safely decoupled from the holder 7, while remaining stably attached to the hub 32 (FIG. 10). Accordingly, at the end of the loading method carried out by the loading system 1, in embodiments the result is that of a delivery instrument 30 featuring two deployment elements, one provided by the receiver 33, the other provided by the receiver 4 that was formerly part of another device, wherein both deployment elements can be controlled by the instrument 30. The inflow portion of the prosthesis 2 is held radially collapsed by the receiver 4, while the outflow portion is held radially collapsed by the receiver 33. The portion of the armature in between the inflow and outflow portion is instead left free of radial contraction by the deployment elements, in a way similar to the subject of European Patent no. EP 2 238 947 B1 in the name of the same Applicant, which is hereby incorporated by reference herein.

By way of summary, in embodiments, a method is defined of loading a prosthetic heart valve onto a delivery instrument by means of a loading system 1 including the delivery instrument 30 as well, the method including:

displacing the gripper 3 from the first axial position I to the second axial position II to fit the at least one portion (e.g. the inflow portion) of the heart valve prosthesis 2 into the first receiver 4 in a radially collapsed condition;

decoupling the first funnel shaped element 5 from the loading system 1;

coupling the first receiver 4 to the hub 32 of the delivery instrument 30;

displacing the second receiver 33 from the third axial position III to the fourth axial position IV to fit the second portion (e.g. the outflow portion) of the heart valve prosthesis 2 into the second receiver 33 in a radially collapsed condition;

decoupling the second funnel shaped element 37 from the delivery instrument; and decoupling the first receiver 4 from the holder 7, while maintaining the same attached to the hub 32 of the delivery instrument 30.

While the ideas and principles of the disclosure remain the same, the details of construction and the embodiments may widely vary with respect to what has been described and illustrated purely by way of example, without departing from the scope of the present disclosure.

For example, in embodiments the receiver 4 may be sized and dimensioned to cover the entire axial extension of the prosthesis to be implanted, so that the second receiver 33 may not be necessary. In these embodiments, therefore, the loading system 1 may only include the gripper 3 with the prosthesis 2 attached thereto, the related actuation facilities (i.e. the tubular member 6 with the drive member 12, for instance), the first receiver dimensioned as above, and the first funnel shaped element 5. In some embodiments, displacement of the gripper 3 from the first axial position I to the second axial position II results in the loading of the entire prosthesis into the receiver 4. Detachment of the gripper 3 from the prosthesis may occur just as disclosed above, but the full-length receiver 4 can be coupled to a delivery instrument later, as the delivery instrument is no longer required to complete the loading action.

In some embodiments the receiver 4 may be provided with an annular portion extended in length as a delivery sheath, which may be intended to cover the axial length of the prosthesis 2, and which may be axially slidable relative to the hub 28. Accordingly, the hub 28 and the annular portion 26 may have two separate coupling interfaces with the delivery instrument: one for the hub, intended to mate with a static portion of the shaft of the delivery instrument, the other for the sheath 26, intended to mate with an actuation member of the delivery instrument for axial displacement thereof.

Additionally, in embodiments disclosed herein the inflow portion of the prosthesis 2 is referred to pre-mounted on the gripper and later sitting in the receiver 4, while the outflow portion of the prosthesis is referred to as coupling sitting into the second receiver 33, in other embodiments they may be arranged the other way around, i.e. with the inflow portion sitting in the receiver 33, and the outflow portion pre-mounted on the gripper and later sitting in the receiver 4. In this regard, when the distal portions 120 of the arched struts 108 are provided with a hairpin shape, the same may provide a natural engagement site for the gripper 3, and specifically for the resilient fingers 20.

In any case, loading of the prosthesis onto a receiver element to be later used as part of a delivery instrument can be performed smoothly and efficiently, and most of all with a device that may come ready out of the jar wherein the prosthesis 2 is stored, thereby greatly simplifying the manipulation of heart valve prosthesis from the jar to the delivery instrument.

While the ideas and principles of the disclosure remain the same, the details of construction and the embodiments may widely vary with respect to what has been described and illustrated purely by way of example, without departing from the scope of the present disclosure.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

The invention claimed is:

1. A loading system for a heart valve prosthesis including a radially contractible armature and a prosthetic heart valve coupled to said armature, said armature having at least one radially contractible annular portion, the loading system comprising:

a gripper that is axially operable along a longitudinal axis (XI) of the loading system from a first axial position (I) to a second axial position (II), wherein in the first axial position (I) the gripper engages the heart valve prosthesis with the armature in a radially expanded condition;

a first receiver for the heart valve prosthesis, the first receiver being configured for holding at least a first portion of the heart valve prosthesis in a radially contracted condition upon engagement of the first receiver by the heart valve prosthesis, and wherein the gripper is axially displaceable relative to the first receiver;

a first funnel shaped element surrounding the first receiver, the first funnel shaped element having a first diameter (D1) and a second diameter (D2), the second diameter (D2) being smaller than the first diameter (D1) and being arranged axially closer to the first receiver than the first diameter (D1), and wherein the gripper is axially displaceable relative to the first funnel shaped element; and a tubular member which is axially fixed relative to said gripper, the tubular member including a holder to which the first receiver is mated, the tubular member including a driver member configured to provide an axial displacement to the gripper so as to displace the heart valve prosthesis axially through the first funnel shaped element from the first diameter (D1) to the second diameter (D2), so as to provide a radial contraction of the armature of the heart valve prosthesis and a fitting of said at least a first portion into said first receiver in a radially contracted condition upon reaching the second axial position (II), wherein the receiver, the gripper, and the heart valve prosthesis attached thereto are stored in a jar (J) filled with a preservation solution, the first funnel shaped element being pre-mounted on the first receiver.

2. The loading system of claim 1, wherein the gripper includes a stud encased by said tubular member and a gripping portion at one end of the stud, the driver member engaging the stud to provide an axial displacement thereof upon operation of the driver member, the gripping portion engaging coupling elements of the at least a first portion of the heart valve prosthesis in the first axial position (I).

3. The loading system of claim 2, wherein the stud is threaded, and wherein the drive member is a threaded rotary drive member engaging the thread of the stud.

4. The loading system of claim 2, wherein said stud is a hollow stud and includes an axial slot, wherein the holder extends axially along and coaxially to the longitudinal axis (XI) and within the tubular member, wherein the hollow stud is slidably fitted around the holder, and wherein the axial slot accommodates a bridge member connecting the holder to the tubular member.

5. The loading system of claim 1, wherein the gripper includes a gripping portion comprising a plurality of resilient finger members, the resilient finger members engaging the heart valve prosthesis radially outwardly of the heart valve prosthesis, and being radially displaceable from a radially divaricated condition to a radially collapsed condition upon an axial displacement of the gripper relative to the first funnel shaped element from the first axial position (I) to the second axial position (II), thereby providing the radial contraction of the armature of the heart valve prosthesis.

6. The loading system of claim 5, wherein each resilient finger is associated to a guide blade, each guide blade including a longitudinal through slot configured to accommodate the resilient finger during a displacement of the resilient finger from the radially divaricated to the radially collapsed condition, thereby keeping the same aligned along a longitudinal direction (XI).

7. The loading system of claim 1, wherein the first funnel shaped element is detachably coupled to the first receiver.

8. The loading system of claim 1 further comprising a delivery instrument for the heart valve prosthesis, the delivery instrument including a shaft, a hub carried by said shaft, and a second receiver which is axially slidable relative to the hub from a third axial position (III) to a fourth axial position (IV), wherein:
the hub of the delivery instrument is configured for coupling with the first receiver;
the second receiver includes a second funnel shaped element coupled thereto, the second funnel shaped element having a third diameter (D3) and a fourth diameter (D4), the fourth diameter (D4) being smaller than the third diameter (D3) and being axially closer to the second receiver than the third diameter (D3), the third diameter (D3) being presented with the heart valve prosthesis coupled to the gripper; and
further wherein in an axial displacement of the second receiver from the third axial position (III) to the fourth axial position (IV) the second funnel shaped element moves relative to the heart valve prosthesis so that a second portion of the armature negotiates a lumen narrowing from the third diameter (D3) to the fourth diameter (D4), and fits into the second receiver in a radially contracted condition.

9. The loading system of claim 8, wherein the second funnel shaped element is detachably coupled to the second receiver.

10. The loading system of claim 1, wherein the loading system further includes a prosthetic heart valve carried by said armature, said armature having at least one radially contractible annular portion, wherein in the first axial position (I) the gripper engages the heart valve prosthesis with the armature in a radially expanded condition.

11. The loading system of claim 5, wherein in the second axial position (II) the resilient fingers are located axially outside of the first receiver and held in a radially contracted condition by the tubular member, wherein axially displacing the gripper back towards the first axial position releases the resilient fingers from the radial contraction action of the tubular member, thereby releasing the resilient fingers from coupling elements of the at least a first portion of the heart valve prosthesis with a radially outward motion thereof relative to the coupling elements.

12. A method of loading a prosthetic heart valve onto a delivery instrument using the loading system according to claim 8, the method including:
displacing the gripper from the first axial position (I) to the second axial position (II) to fit at least one portion of the heart valve prosthesis into the first receiver in a radially collapsed condition;
decoupling the first funnel shaped element from the loading system;
coupling the first receiver to the hub of the delivery instrument;
displacing the second receiver from the third axial position (III) to the fourth axial position (IV) to fit the second portion of the heart valve prosthesis into the second receiver in a radially collapsed condition;
decoupling the second funnel shaped element from the delivery instrument;
decoupling the first receiver from the holder, while maintaining the first receiver attached to the hub of the delivery instrument.

13. The method of claim 12, wherein decoupling the first receiver from the holder comprises axially displacing the gripper, with the at least a portion of the prosthesis loaded into the first receiver, back towards the first axial position to release the gripper from the prosthesis.

14. A method of loading a prosthetic heart valve onto a delivery instrument using the loading system according to claim 1, the method including:
displacing the gripper from the first axial position (I) to the second axial position (II) to fit the heart valve prosthesis into the first receiver in a radially collapsed condition;
decoupling the first funnel shaped element from the loading system,
detaching the first receiver and coupling the first receiver to a delivery instrument.

15. The method of claim 14, wherein the first receiver includes an annular portion extended in length as a delivery sheath, and axially slidable relative to a hub, the annular portion extended in length being configured to cover an axial extension of the prosthesis.

16. The method of claim 15, wherein the annular portion is intended to mate with actuation member of the delivery instrument for axial displacement thereof, and the hub is intended to mate with a static portion of a shaft of the delivery instrument.

* * * * *